(12) United States Patent
Sushkov et al.

(10) Patent No.: US 9,891,297 B2
(45) Date of Patent: Feb. 13, 2018

(54) MAGNETIC SENSING AND IMAGING USING INTERACTIONS BETWEEN SURFACE ELECTRON SPINS AND SOLID STATE SPINS

(71) Applicant: President and Fellows of Harvard College, Cambridge, MA (US)

(72) Inventors: Alexander Sushkov, Cambridge, MA (US); Igor Lovchinsky, Cambridge, MA (US); Nicholas Chisholm, Cambridge, MA (US); Ronald L. Walsworth, Newton, MA (US); Hongkun Park, Lexington, MA (US); Mikhail D. Lukin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 489 days.

(21) Appl. No.: 14/657,593

(22) Filed: Mar. 13, 2015

(65) Prior Publication Data

US 2016/0266220 A1 Sep. 15, 2016

(51) Int. Cl.
*G01V 3/00* (2006.01)
*G01R 33/32* (2006.01)
*G01N 24/12* (2006.01)

(52) U.S. Cl.
CPC .......... *G01R 33/323* (2013.01); *G01N 24/12* (2013.01)

(58) Field of Classification Search
USPC ........................................................ 324/304
See application file for complete search history.

(56) References Cited

U.S. PATENT DOCUMENTS

2015/0253355 A1\* 9/2015 Grinolds .............. G01R 33/022
850/40
2017/0038411 A1\* 2/2017 Yacobi ................... G01Q 60/52

OTHER PUBLICATIONS

Childress, L., et al., "Coherent Dynamics of Coupled Electron and Nuclear Spin Qubits in Diamond," Science, vol. 314, pp. 281-285 (Oct. 13, 2006).
Grinolds, M. S., et al., "Subnanometre resolution in three-dimensional magnetic resonance imaging of individual dark spins," Nature Nanotechnology, vol. 9, pp. 279-284 (Apr. 2014).

(Continued)

*Primary Examiner* — Rodney Fuller
(74) *Attorney, Agent, or Firm* — Wilmer Cutler Pickering Hale and Dorr LLP

(57) ABSTRACT

Systems and methods for magnetic sensing and imaging include a sensor having a network of isolated electron-spin quantum bits (qubits) disposed on the surface of the sensor; and a solid state electronic spin system disposed below the surface of the sensor, wherein the solid state electronic spin system has a spin-state dependent fluorescence; a source of light; a source of first external perturbation, wherein the source of first external perturbation generates a magnetic field; a source of second external perturbation; wherein, the source of light and the first and second external perturbations are configured to coherently and independently manipulate the spin states of at least one qubit and at least one solid state electronic spin system; and a detector to optically measure the solid-state electronic spins spin-state dependent fluorescence.

41 Claims, 21 Drawing Sheets

(56) References Cited

OTHER PUBLICATIONS

Grotz, B., et al., "Sensing external spins with nitrogen-vacancy diamond," New Journal of Physics, vol. 13, 055004, pp. 1-7 (2011).
Laraoui, A., et al., "High-resolution correlation spectroscopy of $^{13}C$ spins near a nitrogen-vacancy centre in diamond," Nature Communications, vol. 4, No. 1651, pp. 1-7 (Apr. 3, 2013).
Myers, B. A., et al., "Probing Surface Noise with Depth-Calibrated Spins in Diamond," Physical Review Letters, vol. 113, pp. 027602-1-027602-6 (Jul. 11, 2014).
Neumann, P., et al., "Quantum register based on coupled electron spins in a room-temperature solid," Nature Physics, vol. 6, pp. 249-253 (Apr. 2010).
Ramsey, Norman F., "A Molecular Beam Resonance Method with Separated Oscillating Fields," Physical Review Letters, vol. 78, No. 6, pp. 695- 699 (Jun. 15, 1950).
Rosskopf, T., et al., "Investigation of Surface Magnetic Noise by Shallow Spins in Diamond," Physical Review Letters, vol. 112, pp. 147602-1-147602-5 (Apr. 11, 2014).
Schaffry, M., et al., "Proposed Spin Amplification for Magnetic Sensors Employing Crystal Defects," Phys. Rev. Lett., vol. 107, pp. 207210-1-207210-5 (Nov. 11, 2011).
Sushkov, A. O., et al., "Magnetic resonance detection of individual proton spins using a quantum reporter network," Department of Physics, Harvard University, pp. 1-5 (Oct. 14, 2014).

\* cited by examiner

MAGNETIC SENSING AND IMAGING USING INTERACTIONS BETWEEN SURFACE ELECTRON SPINS AND SOLID STATE SPINS

STATEMENT OF GOVERNMENT RIGHTS

This invention was made with government support under Grant No. HR-0011-11-C-0073 awarded by the Defense Advanced Research Projects Agency (DARPA). The government has certain rights in this invention.

BACKGROUND

Nuclear magnetic resonance (NMR) and magnetic resonance imaging (MRI) are essential tools for both the physical and life sciences, but have been limited to the detection of large ensembles of spins due to their low sensitivity, or the macroscopic nature of sensors. It is desirable to push this sensitivity to its ultimate physical limit, the detection of individual nuclear spin signals localized in a small volume.

SUMMARY OF THE INVENTION

In an aspect, a system includes a sensor, wherein, the sensor includes, a network of isolated electron-spin quantum bits (qubits) that act as quantum reporter spins disposed on the surface of the sensor; and a solid state electronic spin system disposed below the surface of the sensor, wherein the solid state electronic spin system has a spin-state dependent fluorescence; a source of light; a source of first external perturbation, wherein the source of first external perturbation generates a magnetic field; a source of second external perturbation; wherein, the source of light and the source of first and second external perturbation are configured to coherently and independently manipulate the spin states of at least one qubit and at least one solid state electronic spin system; and a detector to optically measure the change in solid-state electronic spins spin-state dependent fluorescence.

In some embodiment, the sensor includes a high purity diamond crystal lattice. In some other embodiments, the solid state electronic system is a nitrogen-vacancy (NV) spin in the high purity diamond lattice.

In some embodiments, the source of second external perturbation is an radio frequency (RF) electromagnetic field source. In some other embodiments, the source of second external perturbation is an electronic spin resonance (ESR) field source.

In some embodiments, the detector is a CCD camera, or a photomultiplier, or a photodiode.

In some embodiments, the sample to be measured is placed in contact with the surface of the sensor. In some other embodiments, the sample to be measured is placed in the proximity of the sensor.

In some embodiments, the solid state electronic spin system interacts with one quantum reporter spin. In some other embodiments, the solid state electronic spin system interacts with multiple quantum reporter spins.

In some embodiments, the solid state spin systems spin-dependent fluorescence is changed due to the interaction with the quantum reporter spin.

In some embodiments, the source of light radiation is an optically pumped laser. In some other embodiments, the optically pumped laser has a wavelength of 532 nm.

In an aspect, a method of manipulating the reporter spin network and the solid state electronic spin system, includes, applying a first pulse sequence of external perturbation to a network of isolated electron-spin quantum bits (qubits) disposed on the surface of the sensor and a solid state electronic spin system disposed below the surface of the sensor, wherein the solid state electronic spin system has a spin-state dependent fluorescence; applying a second pulse sequence of external perturbation to the network of isolated electron-spin quantum bits (qubits); applying a third pulse sequence of external perturbation to the network of isolated electron-spin quantum bits (qubits) and a solid state electronic spin system disposed below the surface of the sensor; wherein the first and the third pulse sequence of external perturbations probes the quantum state of at least one electronic-spin quantum bits using at least one shallow state electronic spin system; and wherein, the quantum state of the reporter spin network is manipulated in the second pulse sequence of the external perturbation.

In some embodiments, the method further includes comparing the reporter-spin quantum states during the first and third pulse sequence of external perturbation.

In some embodiments, the method further includes controlling the length of the first and third pulse sequence of external perturbation, wherein the length of the pulse sequence of external perturbation is short enough for the change in the optical fluorescence of the solid state spins to be dominated by the coupling to the proximal most strongly coupled reporter spin. In some other embodiments, the method further includes controlling the length of the first and third pulse sequence of external perturbation, wherein the length of the pulse sequence of external perturbation is long enough for the change in the optical fluorescence of the solid state spins to be dominated by the coupling to multiple reporter spins.

In some embodiments, the first pulse sequence of external perturbation of the solid state electronic spin systems comprises of a $\pi/2$-pulse followed by a $\pi$-pulse which is further followed by a $\pi/2$-pulse.

In some other embodiments, the third pulse sequence of external perturbation of the solid state electronic spin systems comprises of a $\pi/2$-pulse followed by a $\pi$-pulse which is further followed by a $\pi/2$-pulse.

In some embodiments, first pulse sequence of external perturbation of the isolated electron-spin quantum bits (qubits) comprises of a $\pi$-pulse.

In some embodiments, the third pulse sequence of external perturbation of the isolated electron-spin quantum bits (qubits) comprises of a $\pi$-pulse.

In some embodiments, the second pulse sequence of external perturbation of the isolated electron-spin quantum bits (qubits) comprises of a $\pi/2$-pulse, followed by a $\pi$-pulse, which is further followed by a $\pi/2$-pulse.

In an aspect, a method of sensing, coherently coupling and imaging a nuclear spin, includes, providing a sample containing at least one nuclear spin in proximity to a sensor; wherein the sensor comprises a network of isolated electron-spin quantum bits (qubits) that act as quantum reporter spins disposed on the surface of the sensor; and another solid state electronic spin system, wherein the solid state electronic spin system has a spin-state dependent fluorescence; exposing the sensor to light and a first and second external perturbation energy to coherently and independently manipulate at least one electron-spin quantum bit (qubit) and at least one solid state electronic spin system; wherein the interaction of the nuclear spin with the qubit and the interaction of the qubit with the solid state electronic spin system changes the spin-state dependent fluorescence of the solid state electronic spin; detecting the change in the spin-state dependent fluorescence of the solid state electronic spin system; and inferring information regarding the nuclear spins of the sample using the detected change in the spin-state dependent fluorescence of the solid state electronic spins.

In some embodiments, the sensor in the method of sensing, coherently coupling and imaging a nuclear spin includes a high purity diamond crystal lattice. In some embodiments, the solid state electronic spin system is a nitrogen-vacancy (NV) spin in the high purity diamond lattice.

In some embodiments, the information inferred regarding the nuclear spins of the sample in the method of sensing, coherently coupling and imaging a nuclear spin, is spatial data.

In some embodiments, the resolution of the measurement of the nuclear spin in the method of sensing, coherently coupling and imaging a nuclear spin, is in the nano-length scale.

In some embodiments, the second external perturbation energy in the method of sensing, coherently coupling and imaging a nuclear spin wherein includes a radio frequency (RF) electromagnetic field. In some other embodiments, the second external perturbation includes an electronic spin resonance (ESR) field.

In some embodiments, the detector, in the method of sensing, coherently coupling and imaging a nuclear spin, is a CCD camera, or a photomultiplier, or a photodiode.

In some embodiments, the sample is placed in contact with the surface of the sensor in the method of sensing, coherently coupling and imaging a nuclear spin.

In some embodiments, the method of sensing, coherently coupling and imaging a nuclear spin wherein, manipulating at least one electron-spin quantum bit (qubit) and at least one solid state electronic spin system includes, applying a first pulse sequence of external perturbation to a network of isolated electron-spin quantum bits (qubits) that act as quantum reporter spins disposed on the surface of the sensor and a solid state electronic spin system disposed below the surface of the sensor, wherein the solid state electronic spin system has a spin-state dependent fluorescence; applying a second pulse sequence of external perturbation to only the network of isolated electron-spin quantum bits (qubits); applying a third pulse sequence of external perturbation to the network of isolated electron-spin quantum bits (qubits) and a solid state electronic spin system disposed below the surface of the sensor; wherein the first and the third pulse sequence of external perturbations comprises probing the quantum state of at least one electronic-spin quantum bits using at least one shallow state electronic spin system; and wherein, the quantum state of the reporter spin network is manipulated in the second pulse sequence of external perturbation.

In some embodiments, manipulating at least one electron-spin quantum bit and at least one solid state electronic spin system further includes comparing the reporter-spin quantum states during the first and third pulse sequence of external perturbation. In some embodiments, the length of the pulse sequence of external perturbation is short enough for the change in the optical fluorescence of the solid state spins to be dominated by the coupling to the proximal most strongly coupled reporter spin. In some other embodiments, the length of the pulse sequence of external perturbation is long enough for the change in the optical fluorescence of the solid state spins to be dominated by the coupling to multiple reporter spins. In some embodiments, the first pulse sequence of external perturbation of the solid state electronic spin systems includes a $\pi/2$-pulse followed by a $\pi$-pulse which is further followed by a $\pi/2$-pulse. In some other embodiments, the third pulse sequence of external perturbation of the solid state electronic spin systems includes of a $\pi/2$-pulse followed by a $\pi$-pulse which is further followed by a $\pi/2$-pulse. In some embodiments, the first pulse sequence of external perturbation of the electron-spin quantum bits (qubits) includes a $\pi$-pulse. In some other embodiments, the third pulse sequence of external perturbation of the electron-spin quantum bits (qubits) comprises of a $\pi$-pulse. In some other embodiments, the second pulse sequence of external perturbation of the electron-spin quantum bits (qubits) includes a $\pi/2$-pulse, followed by a $\pi$-pulse, which is further followed by a $\pi/2$-pulse.

In some embodiments, the method of sensing, coherently coupling and imaging a nuclear spin, wherein, a plurality of the qubits from the quantum reporter spin network are read out by a plurality of solid state electronic spin system through the change of the spin-state dependent fluorescence.

BRIEF DESCRIPTION OF THE DRAWINGS

The following figures are provided for the purpose of illustration only and are not intended to be limiting.

DETAILED DESCRIPTION

A method and device for magnetic resonance imaging with single nuclear-spin sensitivity under ambient conditions is described.

In an aspect, the device includes a sensor having a network of isolated electronic-spin quantum bits (qubits) that act as quantum reporter spins situated nearby (<5 nm) the sensing target, and another solid state electronic spin system having a spin-state dependent fluorescence located in the proximity of the qubits and below the surface of the sensor but within a range of 1 nm to 30 nm to facilitate interaction with the qubits. The device additionally includes a source of light and a source of first and second external perturbation that allow the device to coherently manipulate the qubits and the solid state electronic spins. The interaction between the spin states of the qubits and solid-state electronic spins alters the spin-state dependent fluorescence of the solid-state electronic spins. The system additionally includes an optical recorder. Optical measurement of the spin-state dependent fluorescence e.g., with a CCD camera or a photomultiplier, or a photodiode, provides information about the nature of the spin interactions. Measurements can be obtained with nano-scale resolution. As discussed in detail below, when the sensor is placed in proximity to a target of interest, the interaction of the target with the spin states of the qubits can be measured as a function of the spin-state dependent fluorescence of the solid-state electronic spins. Changes in the spin-state dependent fluorescence of the solid-state electronic spins can provide information regarding the target of interest, such as location.

Figure 1:
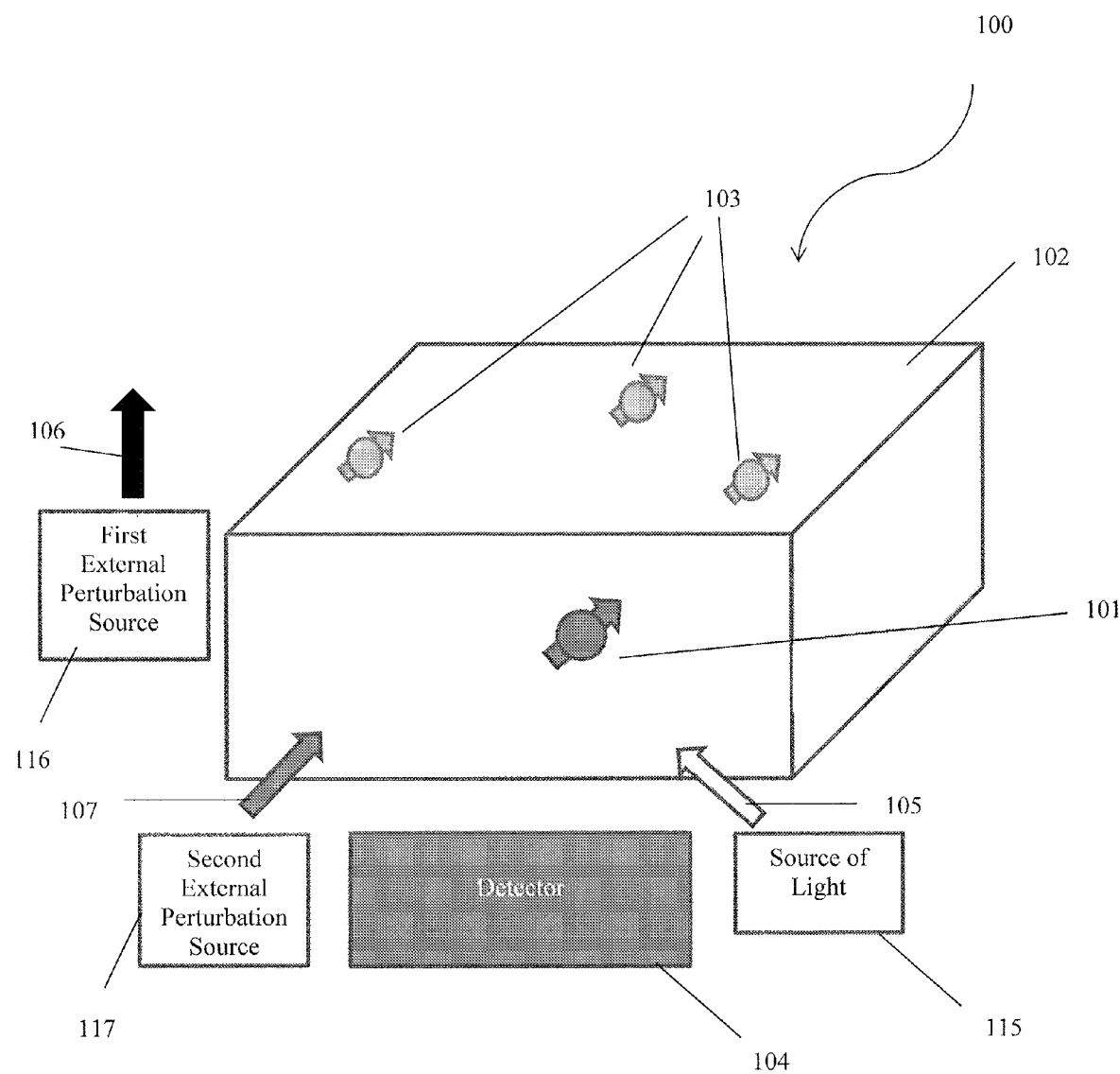
FIG. 1 is a schematic showing a solid state electronic spin system having spin-dependent fluorescence in a sensor, located below the surface of the sensor which also has reporter spins located on the surface of the sensor with a detector used to measure the alteration in the solid-state electronic spin in response to light and a first and second external perturbation originating from a source for each of these.

FIG. 1 is a schematic showing a solid state electronic spin system having spin-dependent fluorescence 101 in a sensor 100, located below the surface 102 of the sensor 100. The sensor also has quantum reporter spins 103 disposed on the surface 102 of the sensor. The schematic also shows a detector 104 used to measure the changes in the solid-state electronic spin in response to light 105, a first external perturbation 106 and a second external perturbation 107 originating from the source of light 115, a first external perturbation source 116, and a second external perturbation 117, respectively.

The light 105 generated from the source of light 115, when applied to the solid state electronic spin system 101, causes the electronic spin to align along one or more well-defined directions. In some embodiments, the source of light 115 is a laser. In an exemplary embodiment, the laser may generate light 105 that has a wavelength of about 532 nm and has green color.

The first external perturbation 106 originating from the first external perturbation source 116 is applied to the solid state electronic spin 101 and causes a detectable splitting in the electronic spin energy level, i.e., causes a detectable Zeeman shift. In some embodiments, the first external perturbation source 116 is a permanent magnet, or a current-carrying coil, and the first external perturbation 106 is a static magnetic field.

A second external perturbation 107 originating from the second external perturbation source 117 is applied to the solid state electronic spin 101 and cause controllable flipping or rotation of the electronic spin. In some embodiments, the external perturbation 107 is a sequence of pulses of RF radiation and the second external perturbation source 117 is an RF field generator. In some other embodiments, the second external perturbation 107 is an electronic spin resonance (ESR) field In an aspect, the sensing device can provide information regarding a target material of interest. By way of example, when an individual nuclear (e.g., proton) spin, such as a can be found in a protein molecule, is placed on the surface of the sensor, the nuclear spin interacts with the electronic spins of the qubits on the sensor surface. The interaction of the quantum reporter network of the qubits with the nuclear spin alters the electronic spin state of the qubits and, thus, their interaction with the solid state electronic spins of the solid-state electronic spins. The changes detected in the spin-state dependent fluorescence of the solid-state electronic spins can be used for sensing, coherent coupling and imaging the nuclear spin with angstrom level resolution. Although the applications apparent to one skilled in the art are innumerable, a non-limiting set of example applications that this approach enables is direct structural imaging of complex molecules that cannot be accessed from bulk studies, a new platform for probing novel materials, monitoring chemical reactions, and manipulation of complex systems on surfaces at a quantum level.

In some embodiments, the sensor is a high purity diamond. In some other embodiments, the solid state electronic spin system is a NV spin. The NV spin is found as a defect in the lattice structure of a single crystal diamond. The NV impurity is based in the lattice of carbon atoms, where two adjacent sites are altered, because one carbon atom is replaced with a nitrogen atom and the other space is left vacant. The vacancies may interact with interstitial atoms, such as nitrogen, and may act as color centers by absorbing visible light. NV spins are visible as red spots when illuminated by laser. In some embodiments, the proximal NV spin is located about 1 nm to 50 nm below the diamond surface.

In some other embodiments, the NV spin is located at about 2 to 50 nm, or 2 to 30 nm, below the diamond surface.

In some embodiments, the method and device describe magnetic sensing and imaging that makes use of a network of electronic spin-½ qubits (quantum reporter spins) on the surface of a high purity diamond crystal. Clean (100) diamond surfaces in ambient conditions host stable electron spins with S=½ and g-factor of 2. Conventionally, these spins have been considered to be deleterious because they are thought to cause decoherence of NV spins within a few nanometers of the diamond surface. Additionally, since the surface electron spins do not emit fluorescence, they cannot be used for measurement of nuclear spin on or near the surface of the diamond. Furthermore, since the NV spins are located a couple of nanometers below the diamond surface and the magnetic field of the nuclear spin is weak and decays rapidly with distance, the sensitivity of using NV spins for direct measurement of the nuclear spins is at best limited.

The method and device described here turns the deleterious surface electron spins in a sensor into a useful resource. With proper control the surface electrons spins can be coherently manipulated and measured optically via a solid state electron spin systems that have spin dependent fluorescence, serving as a network of quantum "reporters" that probe the local magnetic environment. In some embodiments, the solid state electron spins that have spin-dependent fluorescence are NV color centers located a few nanometers below the diamond surface. In some embodiments, the quantum "reporters" are located on the sensor surface and their proximity to the target samples placed on or near the sensor surface, the surface reporter spins dramatically enhance sensitivity and allow for sub nanometer localization of individual nuclear spins.

Figure 2:
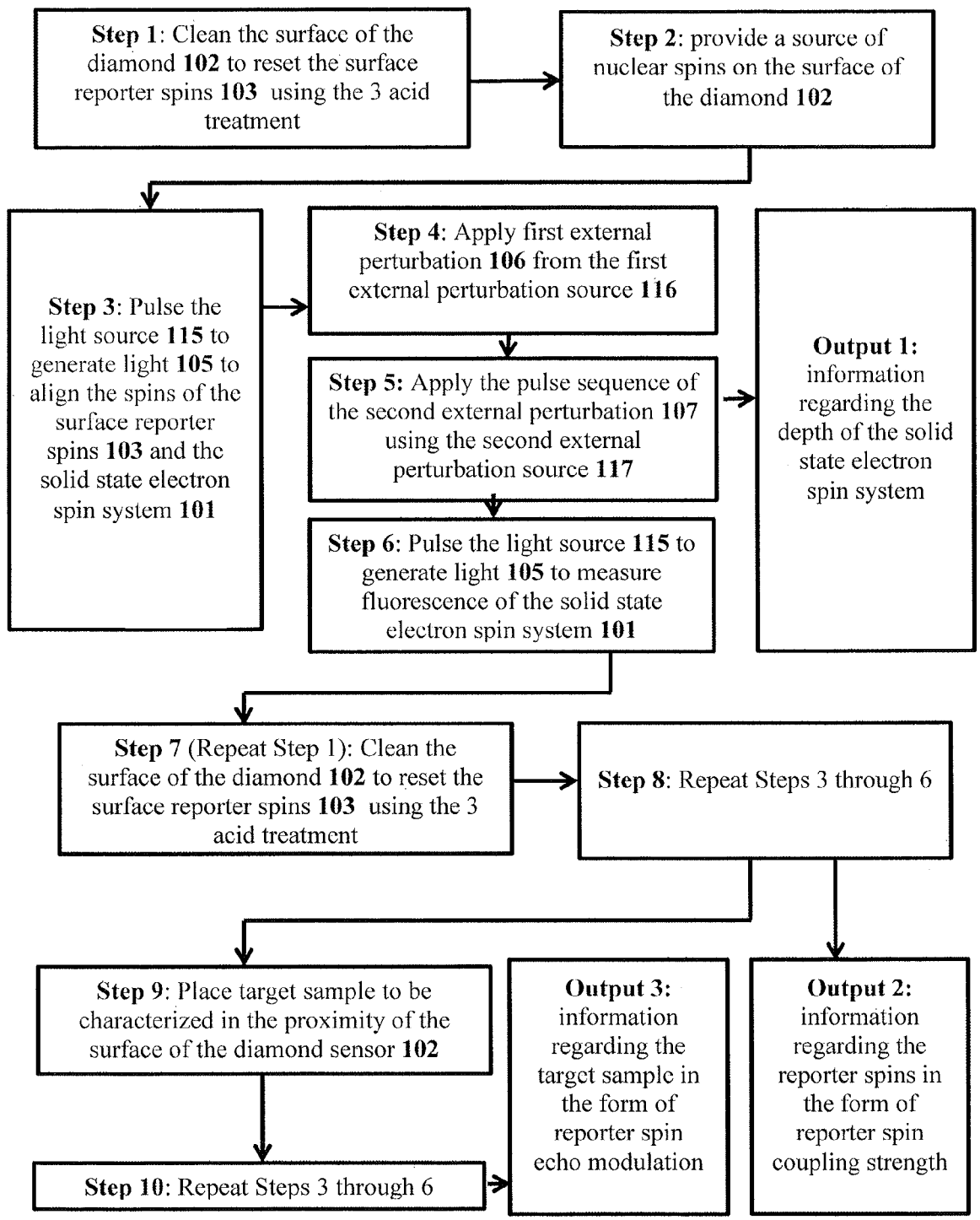
FIG. 2 is a flow chart of steps required for analysis of a stimuli in the proximity of surface electron reporter spins that can change its spin state.

FIG. 2 is a flow chart of steps required for analysis of a stimuli in the proximity of surface electron reporter spins 103 that can change its spin state. Step 1 comprises of cleaning the surface of the diamond 102 to reset the surface reporter spins. In some embodiments this is achieved using a 3 acid treatment described elsewhere in this specification. This followed by Step 2 where a source of nuclear spins is placed on the surface of the diamond 102. Step 3 is then carried out where in the light source 115 is used to generate light 105 to align the spins of the surface report spins. In Step 4, the first external perturbation 106 from the first external perturbation source 116 is applied. This is followed by Step 5, where a pulse sequence of a second external perturbation 107 from second the external perturbation source 117 is applied to the surface reporter spins and the solid state electron spin systems. This is followed by Step 6, where the light source 115 is pulsed to generate light 105 to measure the fluorescence of the solid state electron spin system 101. The measured fluorescence of the solid state electron spin system 101 is used to output information regarding the depth of the solid state electron spin system 101. In Step 7, the surface of the diamond 102 is cleaned to reset the surface reporter spins. In some embodiments this is achieved using a 3 acid treatment described elsewhere in this specification. Followed by the cleaning of the surface of the diamond 102, Steps 3 through 6 are repeated as Step 8. In some embodiments, the pulsing sequence of the second external perturbation 107 from the second external perturbation source 117 in Step 8 is different from the previous pulse sequences of second external perturbation 107 used in Step 5. In some embodiments, the pulsing sequence of the second external perturbation 107 from the second external perturbation source 117 in Step 8 is the same as the previous pulse sequences of second external perturbation 107 used in Step 5. The second pulsing of the light source 115 in Step 8, results in the Output 2 containing information regarding the reporter spins in the form of reporter spin coupling strength. Subsequently, as Step 9, a sample to be characterized is placed on top of or in close proximity to the surface of the diamond 102. As Step 10, Steps 3 through 6 are repeated. In some embodiments, the pulsing sequence of the second external perturbation 107 from the second external perturbation source 117 in Step 10 is different from the previous pulse sequences used earlier. In some embodiments, the pulsing sequence of the second external perturbation 107 from the second external perturbation source 117 in Step 10 is the same as the previous pulse sequences used earlier. The second pulsing of the light source 115 in Step 10, results in the Output 3 containing information regarding the target sample in the form of reporter spin echo modulation. Using Outputs 1, 2 and 3, spatial positioning or imaging of the target sample is obtained.

The method further includes a "reporter pulse sequence" that facilitates probing the reporter spin network on time scales longer that the conventional decoherence times for the shallow solid state electronic spin systems in a sensor. The new "reporter pulse sequence" includes two "probe" segments, in which the shallow solid state electronic spins probes the quantum state of the reporter spin network, separated by an "evolution" segment, in which this state can be manipulated. This pulse sequence facilitates comparison of the reporter-spin quantum states before and after the evolution segment.

Furthermore, by manipulating the duration of the probe segment, it is possible to obtain different and useful information regarding a target. For example, the readout signal of the solid state spins can be dominated by the coupling to the proximal (most strongly coupled) reporter spin when the probe segment is kept short in the timescale of initial DEER collapse, e.g. 1 microsecond, or, include coupling with a plurality of reporter spins in the vicinity of the solid state spin when the probe segment is kept long in the timescale ranging between the timescale of initial DEER collapse and $T_2^{(nv)}$. In an exemplary embodiment, when the solid state spin is an NV center and the probe segment is kept short at around 0.9 µs, the readout signal of the NV center is dominated by the coupling to the proximal (most strongly coupled) reporter spin. One skilled in the art would appreciate that longer probe segments can enable the readout signal of the NV center to cover multiple reporter spins.

Experimental

Diamond Sample

In an exemplary embodiment, the sample used is a polished, single-crystal electronic grade diamond grown by chemical vapor deposition (Element Six), containing substitutional nitrogen and boron in concentrations less than 5 parts per billion (ppb) and 1 ppb respectively. Prior to implantation, the {100} diamond surface was etched approximately 2 µm, using an Ar—$Cl_2$ plasma etch (25 sccm Ar, 40 sccm $Cl_2$, ICP RF 400 W, bias RF 250 W, duration 150 s), followed by an $O_2$ plasma etch (30 sccm $O_2$, ICP RF 700 W, bias RF 100 W, duration 150 s). Nitrogen implantation was done by INNOViON Corporation using a $^{15}N^+$ dosage of $10^9$ $cm^{-2}$ and an implantation energy of 2.5 keV. The implanted diamond was annealed in vacuum using the following procedure: (a) 6 hour ramp to 400° C., (b) 6 hours at 400° C., (c) 6 hour ramp to 800° C., (d) 8 hours at 800° C. and (e) 6 hour ramp to room temperature. After annealing, the diamond was cleaned in a 3-acid mixture (equal volumes of concentrated $H_2SO_4$, $HNO_3$, and $HClO_4$) for two hours under reflux conditions. The same cleaning procedure was used to re-set the locations of the reporter spins on the diamond surface.

Optical Setup

In an exemplary embodiment, a home-built scanning confocal microscope was used to optically address and read out single NV centers. An RF transmission line was fabricated on the surface of a glass coverslip, and the diamond was placed NV-side down on top of this coverslip. The inverted Nikon Plan Fluor 100× oil immersion objective (NA=1.3) was positioned under the coverslip. Its vertical position was controlled with a piezoelectric scanner (Physik Instrumente P-721 PIFOC) and the lateral position of the laser beam focus was controlled with a closed-loop scanning galvanometer (Thorlabs GVS012). Optical excitation was performed with a 532 nm laser (Information Unlimited, MLLIII532-200-1) modulated with an acousto-optic modulator (Isomet Corporation, 1250C-974) in a double-pass configuration. NV center fluorescence was filtered with a 532 nm notch filter (Semrock, NF03-532E) and a 633 nm long-pass filter (Semrock, LP02-633RU) and collected using a single-photon counting module (PerkinElmer, SPCM-AQRH-14-FC). The acousto-optic modulator and the single-photon counting module were gated using TTL pulses produced by a 500 MHz PulseBlasterESR-PRO pulse generator from Spincore Technologies. Typical NV center fluorescence count rate was 20 kHz, and photon counter acquisition window for each sequence repetition was 500 ns.

RF Setup

In an exemplary example, the RF tones, used to address the NV centers and the surface reporter spins, were generated by two Stanford Research SG384 signal generators. The IQ modulation inputs were used to control the x and y quadrature amplitudes of the generator that addressed the NV center. The RF pulses in each channel were generated by the switches (MiniCircuits ZASWA-2-50DR+), controlled by the TTL pulses from the PulseBlasterESR-PRO, and power boosted by an amplifier (three amplifiers were used, depending on the frequency: MiniCircuits ZHL-20W-13+, ZHL-30W-252-S+, and ZHL-16W-43-S+). The two RF channels were combined using an MCLI PS2-109 power splitter, and coupled into the 50Ω-terminated RF transmission line with the diamond sample on top.

Figure 3A:
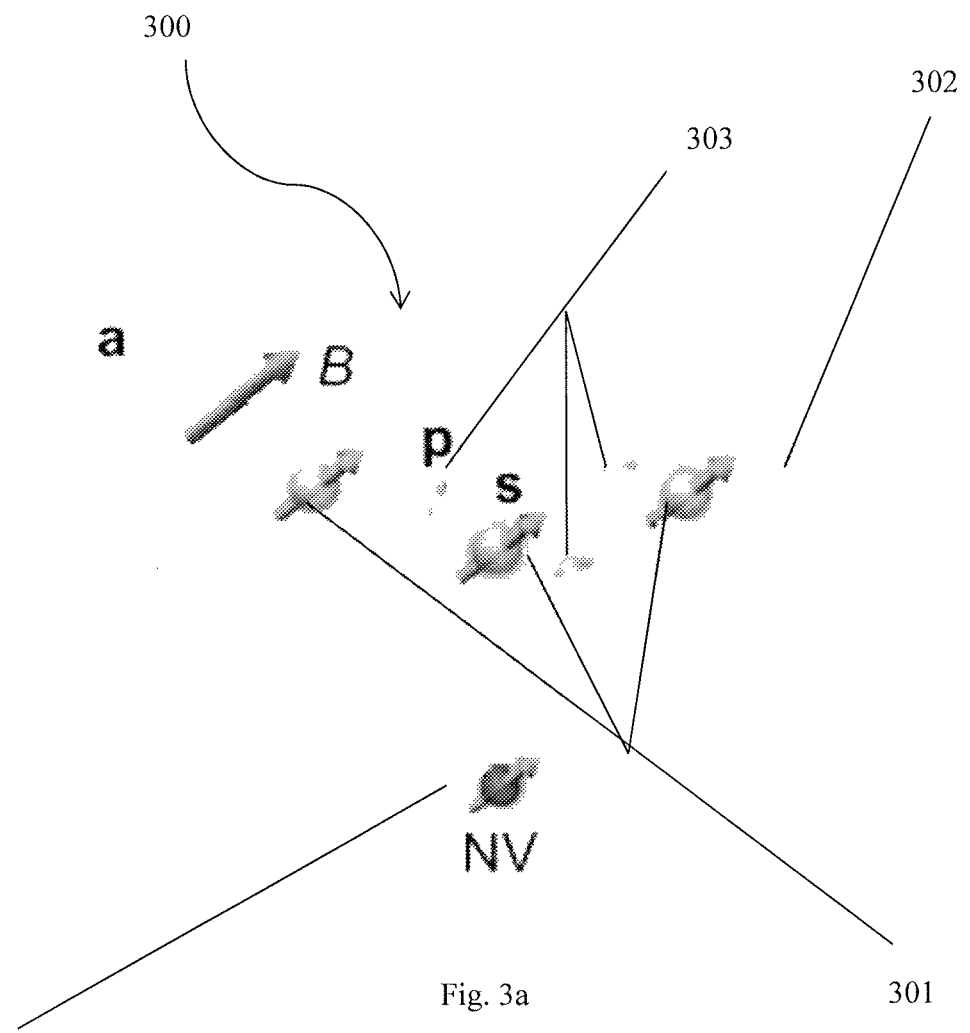
FIG. 3a a schematic of an exemplary embodiment with a network of reporter electron spins, s, on the surface of a diamond crystal, that can be used to detect and localize surface proton spins, p using a single shallow NV center that reads out the quantum states of nearby surface reporter spins through the NV-reporter magnetic dipole interaction.

FIG. 3a, a schematic of an exemplary embodiment with a network of reporter electron spins, s 301, on the surface of a diamond crystal 302, that can be used to detect and localize surface proton spins, p 303, e.g., from a target molecule. A single shallow NV center 304 is used to read out the quantum states of nearby surface reporter spins 301 through the NV-reporter magnetic dipole interaction. The strength of the magnetic dipole coupling between the NV center and the surface spin network was characterized using the DEER pulse sequence.

The dipole-dipole interaction Hamiltonian between the NV center spin S and the surface reporter spin J is:

$$H_d = \frac{\hbar^2 \gamma_e^2}{r_s^3}\left[S \cdot J - 3\frac{(S \cdot r_s)(J \cdot r_s)}{r_s^2}\right], \quad (1)$$

where $r_s$ is the vector from the NV center to the reporter spin. When the magnetic field B is aligned with the NV center axis, all non-secular terms can be neglected, and consider only the terms that commute with $S_z$ and $J_z$:

$$H_d = \frac{\hbar^2 \gamma_e^2}{r_s^3}(1 - 3\cos^2\theta_s)S_z J_z = \hbar k_s S_z J_z, \quad (2)$$

where $\theta_s$ is the angle that vector $r_s$ makes with the magnetic field, and the coupling strength is $$k_s = \frac{\hbar \gamma_e^2}{r_s^3}(1 - 3\cos^2\theta_s). \quad (3)$$

The NV center $|m_s=0\rangle$ state population after the DEER sequence with duration $t_{nv}$ is given by $$S = \frac{1}{2}[1+\cos(k_s J_z t_{nv})] = \frac{1}{2}[1+\cos(k_s \sigma^z t_{nv}/2)], \quad (4)$$

where $\sigma^z = \pm 1$ denotes the sign of the initial projection of the reporter spin.

Tracing over all the reporter spin projections, and, for several reporter spins, adding up the contributions, results in $$S = \frac{1}{2}(1+\langle\cos \varphi_1\rangle), \quad (5)$$

where $\langle\rangle$ denotes averaging over many runs of the experiment (reporter spin projections), and the phase in each run is given by the sum over all reporter spins:

$$\phi_1 = \frac{t_{nv}}{2}\sum_s k_s \sigma_s^z. \quad (6)$$

To perform this average $\langle\sigma_s\rangle=0$, $\langle\sigma_s^z \sigma_{s'}^z\rangle=0$ for $s \neq s'$, $\langle(\sigma_s^z)^2\rangle=1$, which yields $$S = \frac{1}{2}\left[1 + \prod_s \cos(k_s t_{nv}/2)\right]. \quad (7)$$

Figure 3B:
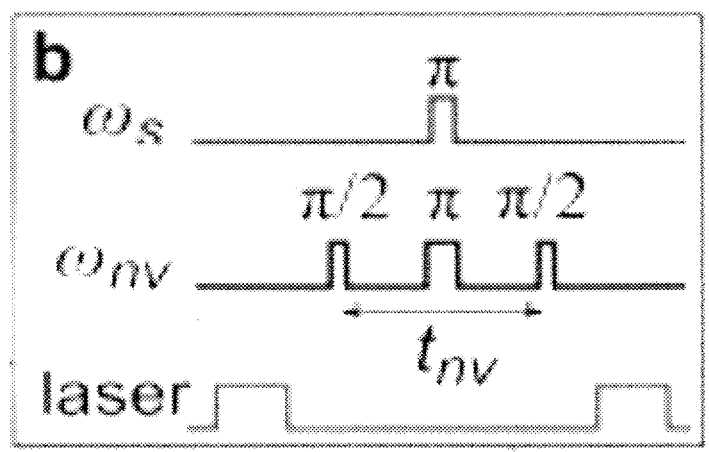
FIG. 3b shows an exemplary DEER sequence.
Figure 3C:
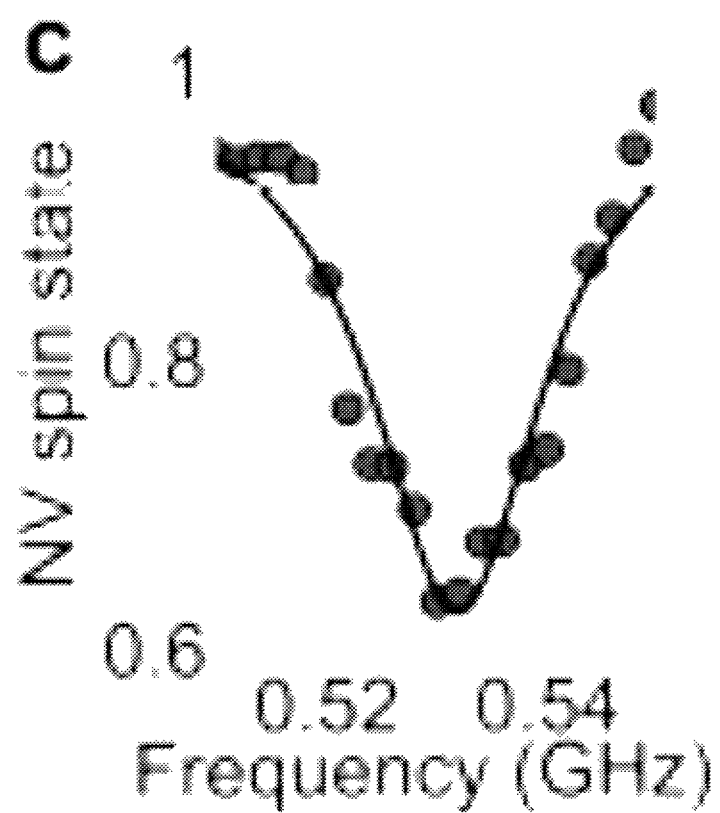
FIG. 3c shows the measured NV double electron-electron resonance (DEER) signal as a function of reporter spin frequency ($\omega_s/2\pi$) for fixed $t_{nv}$.
Figure 3D:
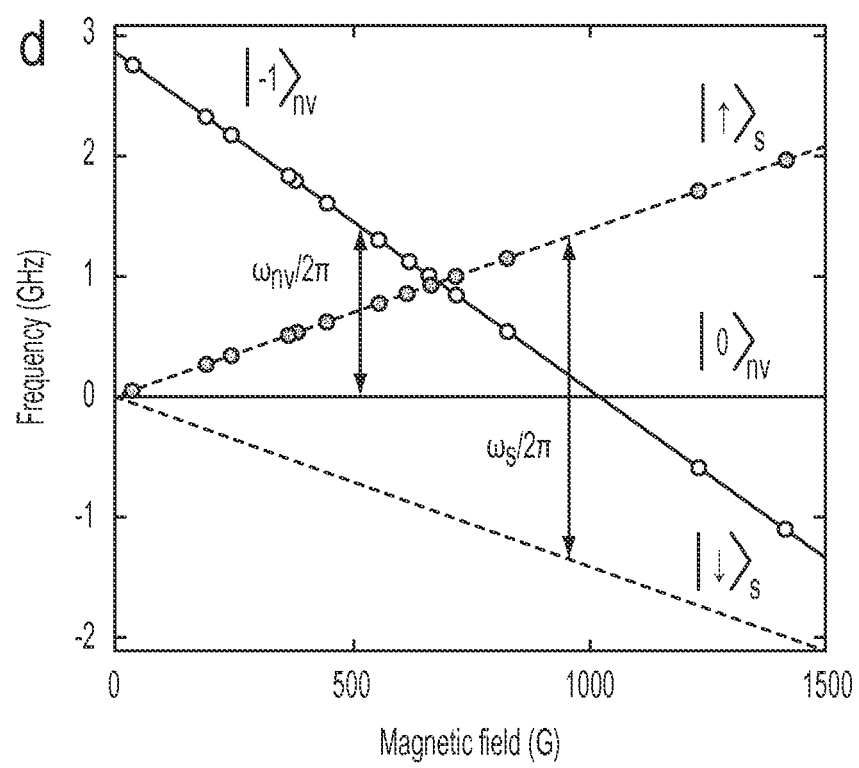
FIG. 3d shows the measured and calculated Zeeman shifts of NV (unfilled circles) and reporter (shaded circles) spin states.

FIG. 3b shows an exemplary DEER sequence. The NV center is initialized into the $m_s=0$ sublevel using an optical pumping laser pulse at 532 nm, and the final quantum state of the NV center is read out using its spin-state-dependent fluorescence, as shown in FIG. 3b. The spin states of the NV center and of the reporter spins are independently manipulated using pulsed magnetic resonance sequences. The $m_s=0 \leftrightarrow m_s=-1$ NV spin transition is addressed at the angular frequency $\omega_{nv}=\Delta-\gamma_e B$, and the $m_s=+\frac{1}{2} \leftrightarrow m_s=-\frac{1}{2}$ surface reporter spin transition is driven at frequency $\omega_s=\gamma_e B$. Here $\Delta=2\pi\times 2.87$ GHz is the NV zero-field splitting, B is the magnitude of the static magnetic field applied along the NV axis, and $\gamma_e=2\pi\times 2.8$ MHz/G is the electron gyromagnetic ratio, as shown in FIGS. 2c and 2d, respectively. FIG. 3c shows the measured NV DEER signal as a function of reporter spin frequency ($\omega_s/2\pi$) for fixed $t_{nv}$. FIG. 3d shows the measured and calculated Zeeman shifts of NV (unfilled circles) and reporter (shaded circles) spin states.

Figure 3E:
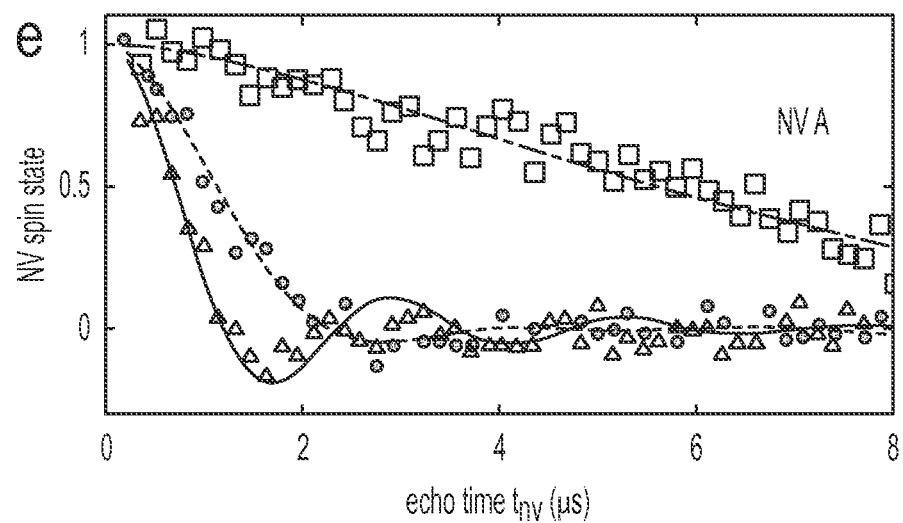
FIG. 3e shows results of DEER experiment with varying echo delay time $t_{nv}$.

FIG. 3e shows results of DEER experiment with varying echo delay time $t_{nv}$. The green squares and line represent the NV center spin echo decay data and fit, respectively. The circles represent the DEER measurements and the triangles represent the DEER measurements after an oxidizing acid treatment. The dashed (----) and solid (-) lines are fits using a model with positions of reporter spins on the diamond surface as fitting parameters. In this and subsequent figures spin state populations are scaled to range between −1 and +1. The NV center (NV A) spin-echo decays on time scale $T_2^{(nv)} \approx 5$ μs, as shown in FIG. 3e; when a π-pulse flips the surface reporter spin population simultaneously with the NV-center π-pulse, the NV-reporter magnetic dipole interaction causes NV spin echo collapse (FIG. 3e, circles), with a form that depends on the locations of the surface spins around the NV center. In some embodiments, because the magnetic dipole interaction is long-range, the NV center can be coupled to multiple surface reporter spins, with the coupling strengths dependent on their positions on the diamond surface. When the diamond was treated with a strongly-oxidizing reflux mixture, such as, equal volumes of concentrated nitric, sulfuric, and perchloric acids for two hours and the DEER experiment was repeated the on the same NV center, the DEER signal was clearly modified (FIG. 3e, triangles), confirming that the reporter spins indeed reside on the diamond surface.

Figure 3F:
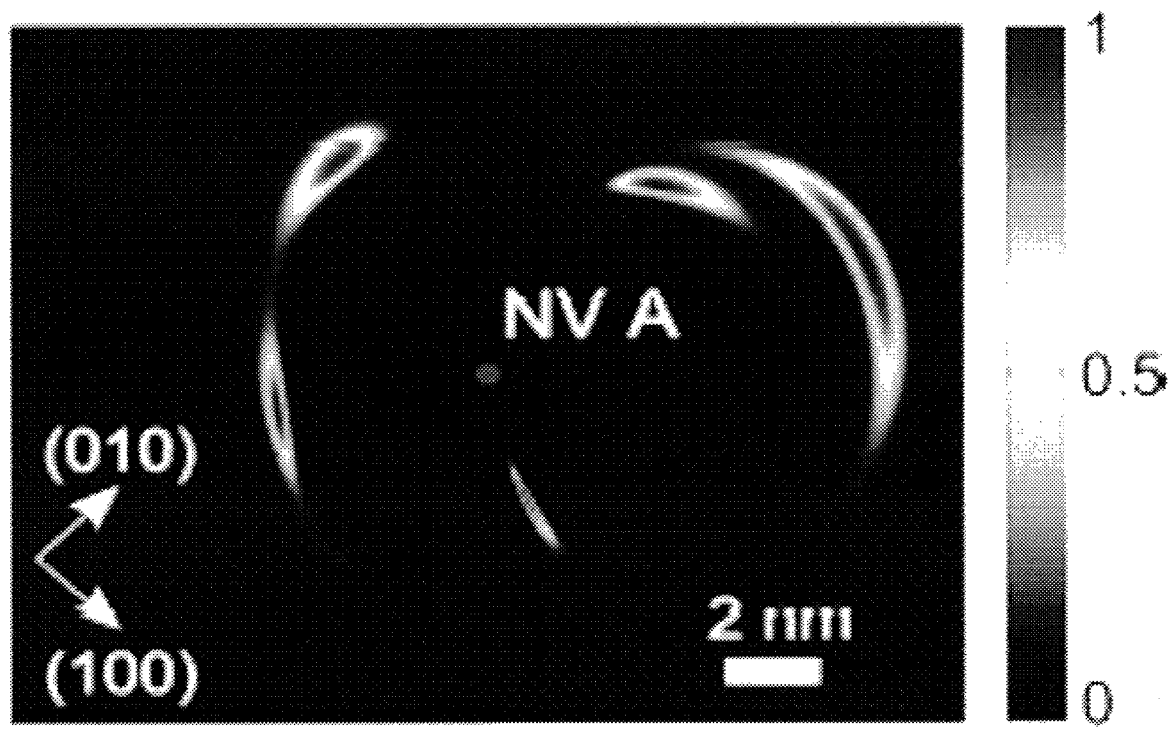
FIG. 3f shows the probability density map for surface reporter spins near NV A, marked by a dot. Arrows mark diamond crystallographic axes; NV center is aligned along (111)

Using this information probability density maps for the surface reporter spins near can be prepared. FIG. 3f shows the probability density map for surface reporter spins near NV A, marked by a dot. Arrows mark diamond crystallographic axes; NV center is aligned along (111).

In order to map the locations of the surface reporter spins, DEER experiments were performed with varying orientation of the magnetic field, using the $\cos^2\theta$ dependence of the dipole interaction. The full Hamiltonian for the system of NV spin-reporter spin coupled via the magnetic dipole interaction is given by:

$$H = \hbar\Delta S_{z'}^2 + \hbar\gamma_e B \cdot S + \hbar\gamma_e B \cdot J + \frac{\hbar^2\gamma_e^2}{r_s^3}\left[S \cdot J - 3\frac{(S \cdot r_s)(J \cdot r_s)}{r_s^2}\right], \quad (8)$$

where $\Delta = 2\pi \times 2.87$ GHz is the zero-field splitting, and the z'-axis points along the NV center symmetry axis.

The zero-field splitting is the largest energy in the problem, therefore making the secular approximation, only the terms that commute with $S_{z'}$ are retained. This amounts to fixing the direction of the vector S to be along the NV center symmetry axis. The next-largest energy term is the reporter-spin Zeeman energy $\hbar\gamma_e B \cdot J$. Once again making the secular approximation, only the terms that commute with $J_{z''}$ are retained, where z" points along the direction of the magnetic field. This amounts to fixing the direction of the vector J to be along the static magnetic field. The magnetic dipole interaction can now be calculated for an arbitrary magnetic field angle. Defining the coordinate axes with the z-axis pointing normal to the diamond surface, and the x axis chosen so that the NV symmetry axis is in the x-z plane. Thus, the unit vector along the NV axis is $(\sqrt{2}, 0, 1)/\sqrt{3}$. In order to map the location of the surface reporter spins, DEER experiments were performed for magnetic field B rotating in the x-y plane by angle φ, relative to the "aligned" direction. Thus the unit vector along the magnetic field is $((\sqrt{2}\cos\varphi, (\sqrt{2}\sin\varphi, 1)\sqrt{3}$. The vector from the NV to the reporter spin is r=(x, y, z), where z is the depth of the NV center, measured as described above. The terms in the dipole interaction Hamiltonian in eqn. (8) can be now be evaluated as:

$$S \cdot J = \frac{2\cos\phi + 1}{3} S_{z'} J_{z''} \quad (9)$$

$$S \cdot r_s = \left(x\sqrt{\frac{2}{3}} + z\sqrt{\frac{1}{3}}\right) S_{z'}, \quad (10)$$

-continued $$J \cdot r_s = \left(x\sqrt{\frac{2}{3}}\cos\phi + y\sqrt{\frac{2}{3}}\sin\phi + z\sqrt{\frac{1}{3}}\right) J_{z''}, \quad (11)$$

and the dipole interaction Hamiltonian:

$$H_d = \quad (12)$$
$$\frac{\hbar^2\gamma_e^2}{r_s^3}\left[\frac{2\cos\phi + 1}{3} - \frac{(x\sqrt{2} + z)(x\sqrt{2}\cos\phi + y\sqrt{2}\sin\phi + z)}{x^2 + y^2 + z^2}\right] S_{z'} J_{z''}$$

Therefore, for a number of reporter spins located at positions $(x_s, y_s)$ on the diamond surface, the NV center spin-state population after a DEER pulse sequence is given by eq. (7), with the coupling strengths $$k_s = \frac{\hbar\gamma_e^2}{r_s^3}\left[\frac{2\cos\phi + 1}{3} - \frac{(x_s\sqrt{2} + z)(x_s\sqrt{2}\cos\phi + y_s\sqrt{2}\sin\phi + z)}{x_s^2 + y_s^2 + z^2}\right] \quad (13)$$

Figure 3G:
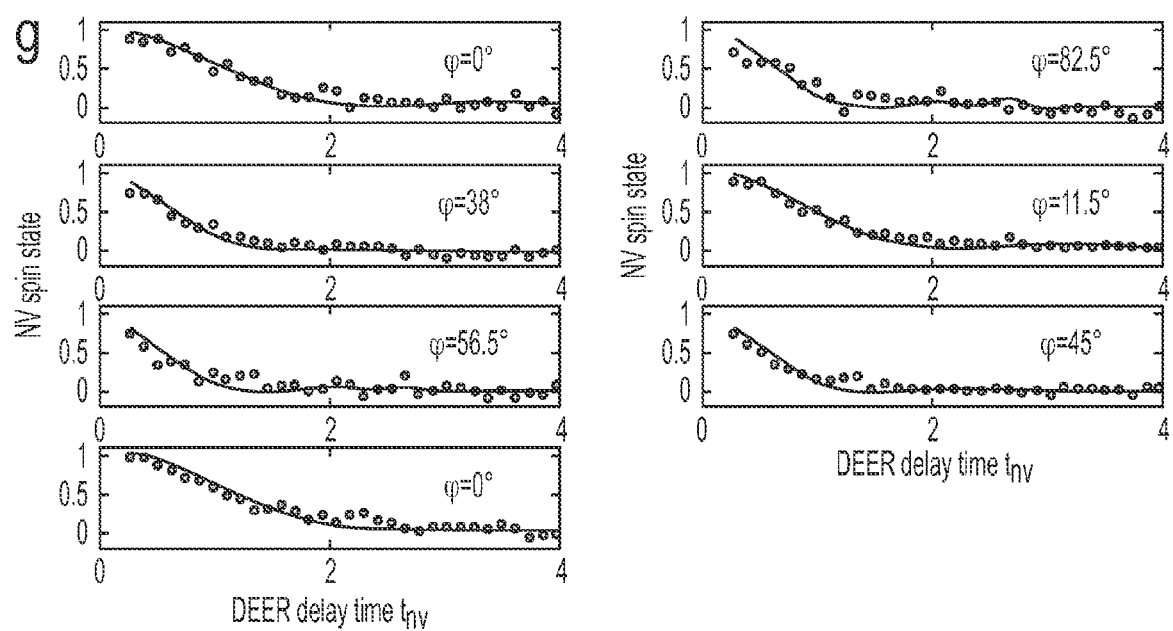
FIG. 3g shows DEER data taken at 7 different magnetic field angles where the magnetic field magnitude was ≈37 G.

The DEER experimental data at 7 different magnetic field angles φ are shown in FIG. 3g. These data were used to produce the probability density map, shown in FIG. 3f, for the positions of 4 proximal reporter spins on the diamond surface near NV A.

In an exemplary embodiment, to determine the reporter spin positions, the DEER measurements are repeated while changing the direction of the applied magnetic field B. The magnetic dipole interaction between the NV center and a surface spin depends on their separation and the angle that the vector between them makes with the vector B. By rotating B, this angle can be changed, and thus the strength of this interaction can be altered. Similar methods have been employed to localize $^{13}C$ spins and other NV centers inside the diamond lattice. By combining the results of the DEER experiments at 7 different magnetic field angles, it was possible to reconstruct the positions of the 4 surface reporter spins nearby the NV center, as shown in FIG. 3f. In FIG. 3f, the color scale represents the reporter spin position probability density (normalized to unity), corresponding to the best-fit chi-squared statistic, performed with each reporter spin position fixed at the associated map coordinate. Advantageously, the above described method allows the surface reporter spin closest to the NV center to be localized with a nanometer-level uncertainty.

Figure 4:
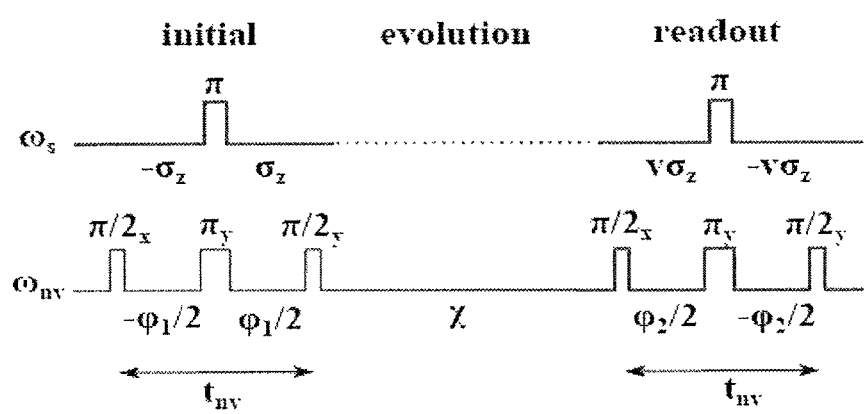
FIG. 4 shows a pulse sequence for NV readout of surface sensors.

In order to manipulate and probe the reporter spin network a "reporter" pulse sequence, inspired by Ramsey interferometry in atomic physics, FIG. 4 is used. FIG. 4 shows a pulse sequence for NV readout of surface sensors. The pulse sequence is separated into two parts: the initial state readout, and the final state readout. During the initial state readout, the phase acquired by the NV center due to the surface sensor spins is φ1, and during the final state readout this phase is φ2. Note that these phases flip sign during the first and second halves of the NV echos, since a π-pulse is applied to the surface sensor spins simultaneously with the π-pulse on the NV. During the period between the initial and the final readout intervals, the NV acquires a phase χ, but, if this time interval is kept longer than NV $T_2^*$, then $\langle\chi\rangle = \langle\sin\chi\rangle = 0$, and χ does not, on average, affect the NV population. The population readout of the NV center at the end of the pulse sequence is then given by $$S = \frac{1}{4}(1 + \cos(\phi_1 + \phi_2) - \cos(\phi_1 - \phi_2)) \quad (17)$$

$$= \frac{1}{2}(1 - \sin\phi_1 \sin\phi_2). \quad (18)$$

Let us assume that the spin projection of a surface sensor spin s at the start of the sequence is $\sigma_s^z$, and the coupling to the NV center is $k_s$, as given in eq. (3). Then the NV phase $\varphi_1$ is given by the sum over all surface sensor spins:

$$\phi_1 = \frac{t_{nv}}{2} \sum_s k_s \sigma_s^z. \quad (19)$$

where $t_{nv}$ is the duration of the echo.

During the surface sensor spin evolution, the projection of the surface sensor spin changes $\sigma_s^z \to v_s^{(i)} \sigma_s^z$, where, for each run i of the experiment $v_s^{(i)} = \pm 1$ (since the spin projection can only take values $\pm 1/2$). After averaging over many experimental runs, average $v_s = \langle v_s^{(i)} \rangle$. For example, if a π-pulse is applied to all surface sensor spins, all $v_s^{(i)} = -1$, and $v_s = -1$. The NV phase $\varphi_2$ is given by $$\phi_2 = \frac{t_{nv}}{2} \sum_s v_s^{(i)} k_s \sigma_s^z. \quad (20)$$

In this way the NV readout provides information about the surface sensor spin evolution $v_s$. Note that the NV population signal has to be averaged over all projections $\sigma_s^z$ of the surface spin sensors.

This average is performed by using $$\langle \sigma_s^z \rangle = 0, \langle \sigma_s^z \sigma_{s'}^z \rangle = 0 \quad (21)$$
for $s \neq s'$, $\langle (\sigma_s^z)^2 \rangle = 1$, $v_s = \langle v_s^{(i)} \rangle$,
to obtain $$S = \frac{1}{2} - \frac{1}{4} \prod_s v_s \sin^2 \frac{k_s t_{nv}}{2}. \quad (22)$$

Figure 5A:
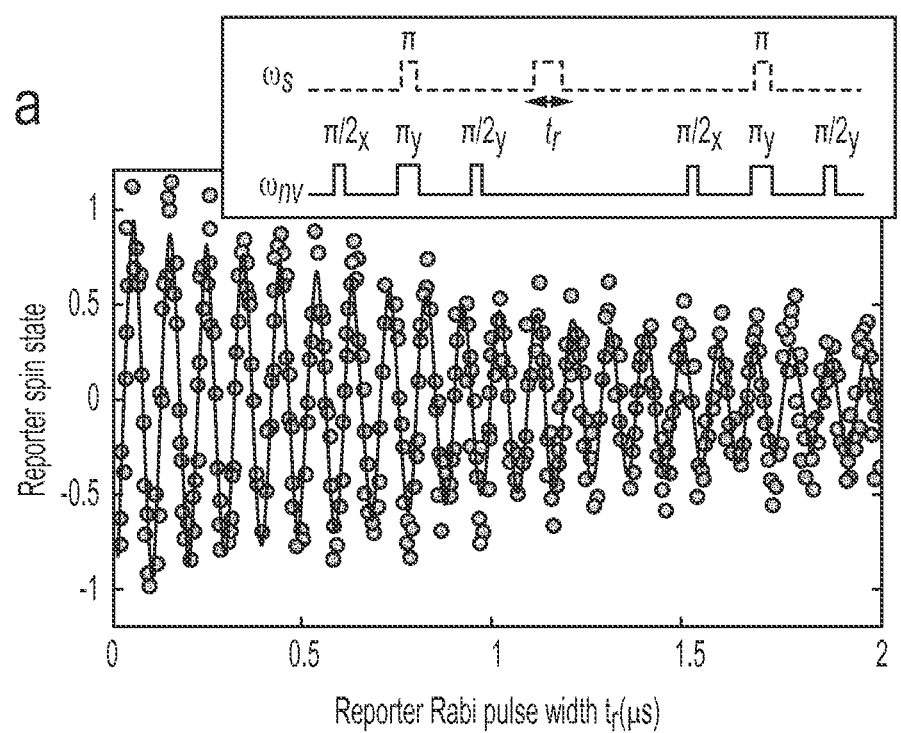
FIG. 5a shows coherent control of reporter spins by varying the length of the radiofrequency (RF) pulse applied at the reporter spin resonance frequency.

The DEER pulse sequence is a useful tool for characterizing the surface reporter spin network on the diamond surface, but it is limited by the decoherence time of the shallow NV center, $T_2^{(nv)}$, which is usually on the order of several microseconds. In order to manipulate and probe the reporter spin network on time scales longer than $T_2^{(nv)}$, the disclosure implements a new "reporter pulse sequence", shown in FIG. 5a, inset. FIG. 5a shows coherent control of reporter spins by varying the length of the radiofrequency (RF) pulse applied at the reporter spin resonance frequency. Rabi oscillations between spin states with a variable-width pulse are shown by the circular points. This data is exponentially-damped fit using the solid line. This protocol, inspired by Ramsey interferometry in atomic physics, consists of two "probe" segments, in which the NV center probes the quantum state of the reporter spin network, separated by an "evolution" segment, in which this state can be manipulated. In essence, this protocol enables the comparison of the reporter-spin quantum states before and after the evolution segment. Importantly, the duration of the evolution segment is limited by the NV center $T_1^{(nv)}$ time, rather than its $T_2^{(nv)}$, thereby extending the evolution timescale by orders of magnitude. In some embodiments, as shown by the measurements described below, the duration of the probe segments was kept short ($\approx 0.9$ μs) to ensure that the NV readout signal was dominated by the coupling to the proximal (most strongly coupled) reporter spin.

Figure 5B:
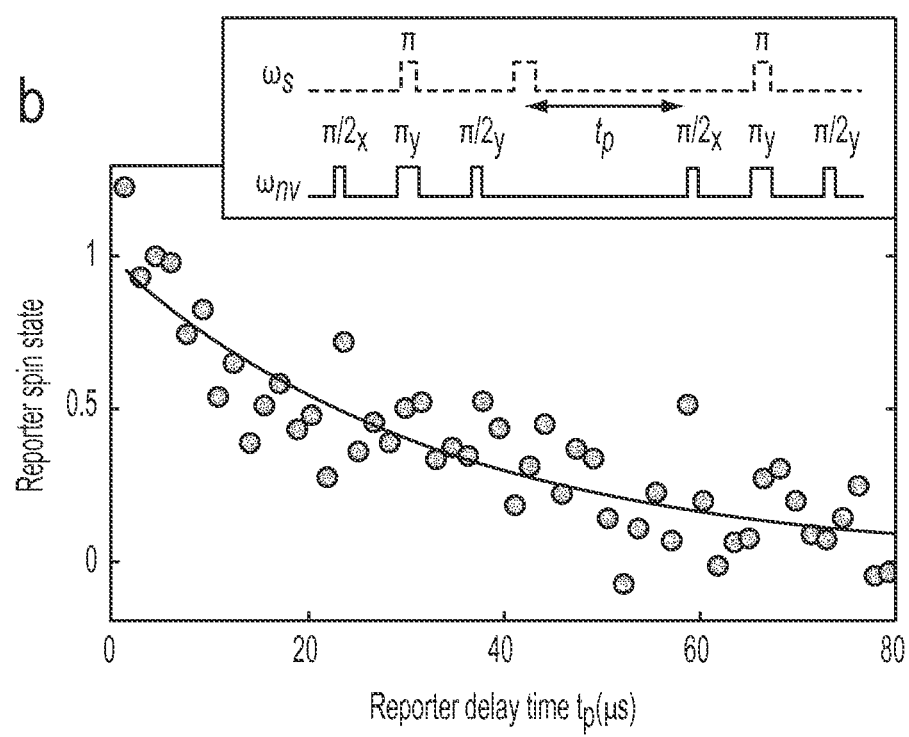
FIG. 5b shows the population relaxation dynamics of the reporter spins (circular points) with an exponential-decay fit (solid line). The inset shows the RF pulse sequence used.

Rabi oscillations with decay time on the order of 1 μs, which is much longer than the reporter-spin Rabi period, are observed, indicating that the pulses can be used for coherent control of the reporter spins. Next, the population relaxation time $T_1^{(s)}$ of the surface spin network was measured by varying the delay time $t_p$ between the two probe segments in the pulse sequence. FIG. 5b shows the population relaxation dynamics of the reporter spins (circular points) with an exponential-decay fit (solid line). The inset shows the RF pulse sequence used. The extracted value of $T_1^{(s)} = (29.4 \pm 2.3)$ μs can be used to place a lower limit of $\approx 5$ nm on the mean separation between the surface reporter spins: because, if these spins were closer together, their mutual magnetic dipole flip-flop interaction would give rise to a shorter population relaxation time. Note that this observation is consistent with the reconstructed spin locations shown in FIG. 3f.

The reporter-spin population relaxation measurements, show in FIG. 5b, can be used to confirm that the reporter spins are well separated on the diamond surface. The rate of flip-flops between neighbor spins, due to magnetic dipole interaction, is given by $$w \approx \frac{\hbar \gamma_e^2}{4s^3} \frac{1}{4}, \quad (14)$$

where s is the separation between them, and the angular factor is approximated, that depends of the magnetic field direction, by unity. For random reporter spin positions there is likely to be a single closest neighbor that dominates the magnetic dipole interaction. If the depth of the NV center z≤s, then the NV center interacts the strongest with a single proximal reporter spin, and the measured population relaxation time $T_1^{(s)}$ corresponds to the time scale for a single spin flip of this proximal reporter:

$$T_1^{(s)} \approx 2\pi/w \approx 32\pi \frac{s^3}{\hbar \gamma_e^2}. \quad (15)$$

If the experimentally-measured $T_1^{(s)} \approx 30$ μs is caused by the magnetic dipole interaction between surface reporter spins, then their separation is s≈5 nm. If another relaxation process limits $T_1^{(s)}$, then s>5 nm.

Another possibility is z>>s, so that the NV center is coupled to many reporter spins. In this case spin diffusion has to be considered, and the population relaxation time $T_1^{(s)}$, as measured by the NV center, would correspond to the time scale for spin diffusion over distance≈z. This can be estimated as follows. The time scale for a single spin flip-flop is given by eq. (15), thus the time scale for diffusion over distance z is:

$$T_1^{(s)} \approx \frac{z^2}{s^2} 32\pi \frac{s^3}{\hbar \gamma_e^2}. \quad (16)$$

If the experimentally-measured $T_1^{(s)} \sim 30$ μs were caused by spin diffusion in a bath of closely-spaced reporter spins, then, from eq. (16), their spacing is extracted to be s≈10 nm. However, for the ≈3.5 nm deep NV centers, this is inconsistent with the assumption z>>s, and it is concluded that z≤s, and s≥0.5 nm, as estimated above.

Detection of the Magnetic Field Created by Protons, Using the Reporter Spins

A. Semiclassical Spin Bath

Figure 6A:
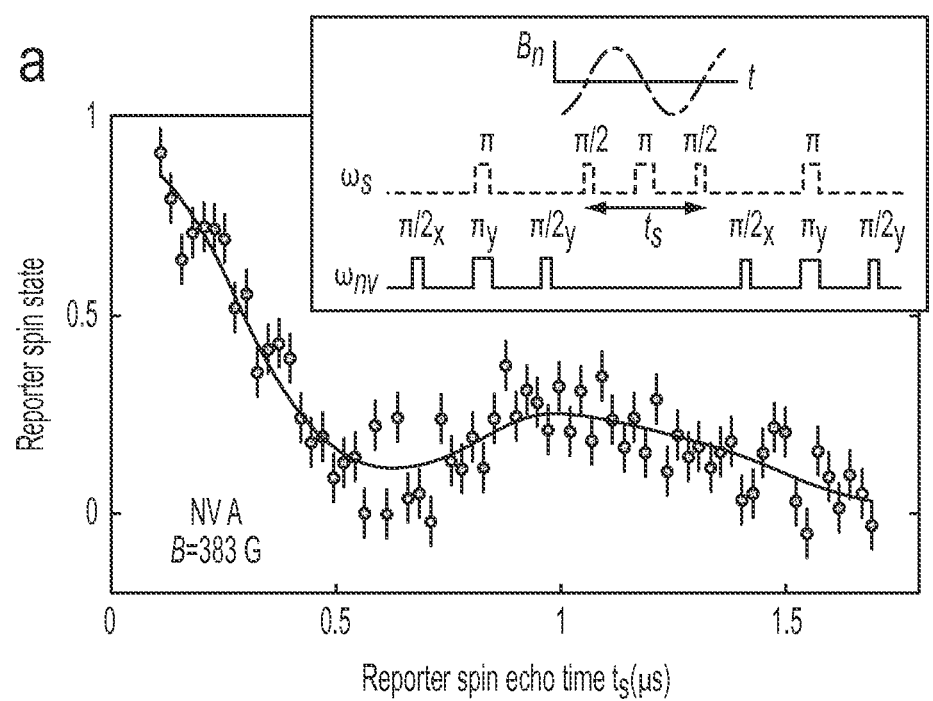
FIG. 6a shows, measurement with NV A of the reporter spin echo modulation at B=383 G (circular points), fit with a model for echo modulation of a reporter spin coupled to a nuclear spin bath (fit shown by a solid line, reduced chi-squared is 1.2) and the inset shows the reporter echo pulse sequence.

In order to measure the surface sensor coupling to proton spins, the pulse sequence shown in FIG. 6a was used with the surface reporter spin echo. A surface reporter spin may be strongly coupled some proximal protons, and weakly coupled to many other protons that are present on the diamond surface. These weakly coupled protons are described as a semiclassical spin bath, whose magnetic moment precesses at the proton Larmor frequency $\omega_n = \gamma_n B$, where $\gamma_n = g_n \mu_N / \hbar$ is the nuclear gyromagnetic ratio. The magnetic moments create a fluctuating magnetic field at the location of the surface sensor spin, and the reporter spin echo modulation due to this fluctuating field is described by the factor $$v_s(t_s) = \exp[-8(\gamma_n^2 B_n^2 / \omega_n^2)\sin^4(\omega_n t_s / 4)], \quad (23)$$

where $B_n$ is the root-mean-squared amplitude of this magnetic field.

In some embodiments, the extracted magnitude of $B_n$ is 0.3 G, which is consistent with the magnitude of the fluctuating magnetic field created by a bath of proton spins, randomly-located on the diamond surface, with mean separation of ≈5.5 Å. The separation between surface OH groups for a (001)-(2×1) hydroxylated diamond surface is predicted to be approximately 2.6 Å. Therefore the measurements are consistent with approximately ¼ of the surfaces sites filled with protons.

B. Coherent Hyperfine Coupling to Individual Nuclear Spins

The hyperfine interaction between a reporter electronic spin and a proton spin can be described by the Hamiltonian $$H = a_0 J \cdot I + \frac{\hbar \gamma_e \gamma_n}{r_n^3}\left[J \cdot I - 3\frac{(J \cdot r_n)(I \cdot r_n)}{r_n^2}\right], \quad (24)$$

where J is the spin operator of the reporter qubit, I is the proton spin operator, $r_n$ is the separation between the surface sensor spin and the nuclear spin, and $a_0$ is the contact hyperfine interaction. In the secular approximation the oscillating terms with $J_x$ and $J_y$ can be neglected, and the Hamiltonian reduces to $H = \hbar a J_z I_z + \hbar b J_z I_x$, where $$a = a_0 + \frac{\hbar \gamma_e \gamma_n}{r_n^3}(1 - 3\cos^2\theta_n), \quad (25)$$

$$b = \frac{\hbar \gamma_e \gamma_n}{r_n^3}(3\cos\theta_n \sin\theta_n), \quad (26)$$

where $\theta_n$ is the angle between the vector between them and the applied magnetic field B. The spin projection of the reporter spin s, coupled to a nuclear spin n, after the echo sequence is described by the expression:

$$v_{s,n}(t_s) = 1 - 2\left(\frac{b\omega_n}{\omega^+\omega^-}\right)\sin^2(\omega^+ t_s / 4)\sin^2(\omega^- t_s / 4), \quad (27)$$

where $$\omega^\pm = \sqrt{(\pm a/2 - \omega_n)^2 + b^2/4}. \quad (28)$$

If the surface sensor is coupled to several proximal nuclear spins, as well as the weakly-coupled nuclear spin bath, then $$v_s(t_s) = \exp[-8(\gamma_n^2 B_n^2 / \omega_n^2)\sin^4(\omega_n t_s / 4)]\prod_n v_{s,n}(t_s). \quad (29)$$

C. Fitting Experimental Data

In addition to the interaction with nuclear spins, the reporter spin decoherence rate $\Gamma_s$ is a fitting parameter. The final expression used for fitting surface spin sensor echo modulation is:

$$v_s(t_s) = e^{-\Gamma_s t_s}\exp[-8(\gamma_n^2 B_n^2 / \omega_n^2)\sin^4(\omega_n t_s / 4)]\prod_n v_{s,n}(t_s), \quad (30)$$

where the product is over the strongly-coupled nuclear spins.

Finally, if the NV center is coupled to several surface sensor spins, $$S = \frac{1}{2} - \frac{1}{4}\prod_s v_s \sin^2\frac{k_s t_{nv}}{2}. \quad (31)$$

as in eq. (22).

Figure 7A:
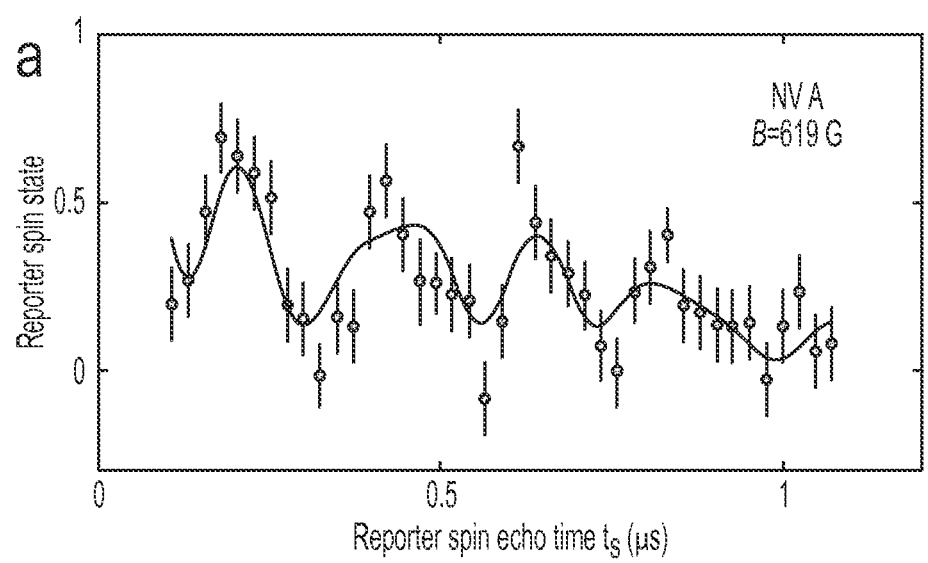
FIG. 7a shows, reporter spin echo modulation for NV A at B=619 G (circular points), and fit using a model with the reporter qubit, proximal to the NV center, coupled to one proton spin (solid line)
Figure 7B:
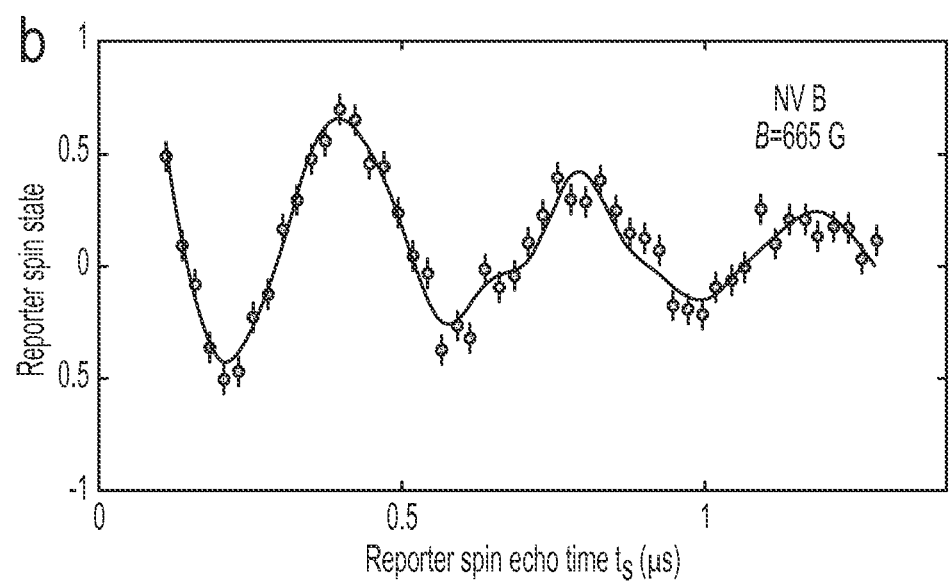
FIG. 7b shows reporter spin echo modulation with NV B at B=665 G (circular points). The best-fit (solid line, reduced chi-squared value of 1.1) corresponds to a model with the reporter qubit, proximal to the NV center, coupled to two proton spins.

The fits shown in FIGS. 7a and 7b were performed by first using the DEER data to extract the magnetic dipole coupling constant $k_s$ of the NV center to the proximal reporter spin, and fitting the reporter spin echo data using eqn. (30), with one or two coherently-coupled protons, and a proton spin bath, see Table I for relevant best-fit parameters for the fits shown FIG. 6a, FIG. 7a, and FIG. 7b.

In order to calibrate the reporter spin state, two measurements were performed using the reporter sequence: (i) with no pulse in the evolution segment, and (ii) with a π-pulse in the evolution segment. These were taken to correspond to (i) no reporter spin state change→+1, and (ii) reporter spin flip→−1. The reporter sequence measurements in this work were done in pairs, with the reporter evolution sequences differing by a reporter π-pulse. For example, the reporter echo measurement was done first with the reporter pulses π/2-π-π/2, immediately followed by a sequence π/2-π-3π/2. It was confirmed that these measurements resulted in opposite final reporter spin populations.

TABLE I

Best-fit parameters.

| NV center | magnetic field | parameter | best-fit value |
|---|---|---|---|
| NV A | 383 G | $k_s$ | 1.6 μs$^{-1}$ |
| | | $\Gamma_s$ | 1.3 μs$^{-1}$ |
| | | $\omega_n$ | 10.6 μs$^{-1}$ |
| | | reduced $\chi^2$ | 1.2 |

TABLE I-continued

Best-fit parameters.

| NV center | magnetic field | parameter | best-fit value |
|---|---|---|---|
| NV A | 619 G | $k_s$ | 1.6 μs$^{-1}$ |
|  |  | $\Gamma_s$ | 1.8 μs$^{-1}$ |
|  |  | $\omega_n$ | 19 μs$^{-1}$ |
|  |  | reduced $\chi^2$ | 1.3 |
| NV B | 665 G | $k_s$ | 1.4 μs$^{-1}$ |
|  |  | $\Gamma_s$ | 1.3 μs$^{-1}$ |
|  |  | $\omega_n$ | 17.1 μs$^{-1}$ |
|  |  | reduced $\chi^2$ | 1.1 |

Figure 6B:
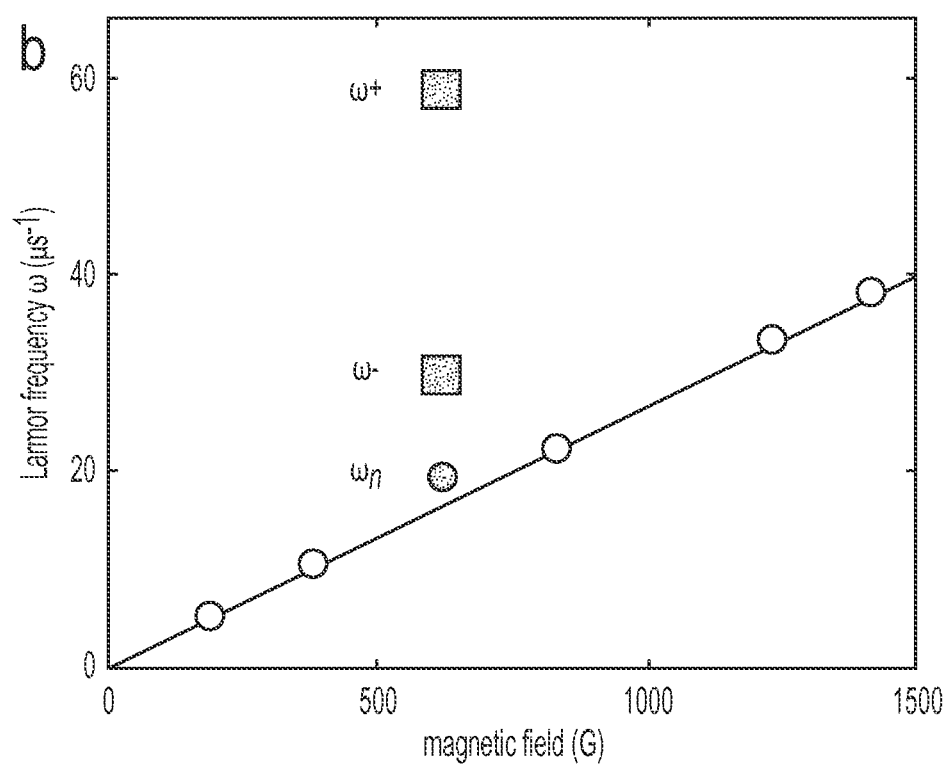
FIG. 6b shows measured values for co, at 5 different settings of the applied static magnetic field (unfilled circular points), consistent with the proton gyromagnetic ratio of $2\pi \times 4.26$ kHz/G (solid line) and the shaded circular point marks the $\omega_n$, and the shaded square points mark the $\omega^-$, and $\omega^+$ oscillation frequencies.

In an exemplary embodiment, using the quantum reporter spin network to perform measurements of the magnetic fields on the diamond surface, using the RF pulse sequence shown in FIG. 6a. FIG. 6a shows, measurement with NV A of the reporter spin echo modulation at B=383 G (circular points), fit with a model for echo modulation of a reporter spin coupled to a nuclear spin bath (fit shown by a solid line, reduced chi-squared is 1.2). The error bars on this and subsequent plots show standard deviations of the data points obtained from averaging approximately 5 million repetitions of the pulse sequence, and are consistent with photon shot noise. The inset shows the reporter echo pulse sequence. The time-varying magnetic field at the site of a reporter spin gives rise to a phase shift during its spin-echo precession time $t_s$, which is converted to a change in its spin state population, and detected by the NV center. By varying the time $t_s$, a frequency filter was implemented, whereby the measurement was sensitive to magnetic-field Fourier components at angular frequencies co on the order of $2\pi/t_s$, showing up as echo collapses at delay times $t_s=2\pi k/\omega$, where k=1, 3, . . . . The experimental data exhibits collapses and revivals characteristic of a time-varying magnetic field created by nuclear spins on the diamond surface, processing in the applied magnetic field B with Larmor frequency $\omega_n=\gamma_n B$, where $\gamma_n$ is the nuclear spin gyromagnetic ratio. FIG. 6a shows an exemplary embodiment of the results for a particular NV center (NV A), and the data are consistent with the reporter spin coupled to an oscillating magnetic field created by surface protons with root-mean-squared amplitude of $B_n$=0.3 G and angular frequency of $\omega_n$=10.6 μs$^{-1}$. In order to determine the nature of these nuclear spins, the measurements were repeated and analyzed at several magnetic fields. FIG. 6b shows measured values for $\omega_n$ at 5 different settings of the applied static magnetic field (unfilled circular points), consistent with the proton gyromagnetic ratio of 2π×4.26 kHz/G (solid line). The shaded circular point marks the $\omega_n$, and the shaded square points mark the $\omega^-$, and $\omega^+$ oscillation frequencies. It was found that the reporter spin echo modulation frequency scales with the applied magnetic field in agreement with the proton gyromagnetic ratio of 2π×4.26 kHz/G (FIG. 6b, unfilled circular points).

Coherent Dynamics Between Individual Reporter and Proton Spins.

Remarkably, however, this simple scaling is not observed at all values of the magnetic field. For example, the data taken with NV A at the magnetic field of 619 G show modulation at frequencies very different from the Larmor frequency expected for the coupling of the reporter spin with a semiclassical proton spin bath (FIG. 6b, shaded points). FIG. 7a shows, reporter spin echo modulation for NV A at B=619 G (circular points), and fit using a model with the reporter qubit, proximal to the NV center, coupled to one proton spin (solid line). This high-frequency modulation, seen in the data plotted in FIG. 7a, signals the presence of coherent dynamics between the reporter and proximal proton spins. In order to reproduce and further explore this coherent coupling, another NV center (NV B) was studied at a similar magnetic field. FIG. 7b shows reporter spin echo modulation with NV B at B=665 G (circular points). The best-fit (solid line, reduced chi-squared value of 1.1) corresponds to a model with the reporter qubit, proximal to the NV center, coupled to two proton spins. The experimental points, shown in FIG. 7b, again display strong modulation, crossing the abscissa axis. This signals coherent population transfer between the proton spin states, mediated by the interaction with a single reporter spin, which cannot occur in the absence of reporter/proton entanglement.

Figure 7C:
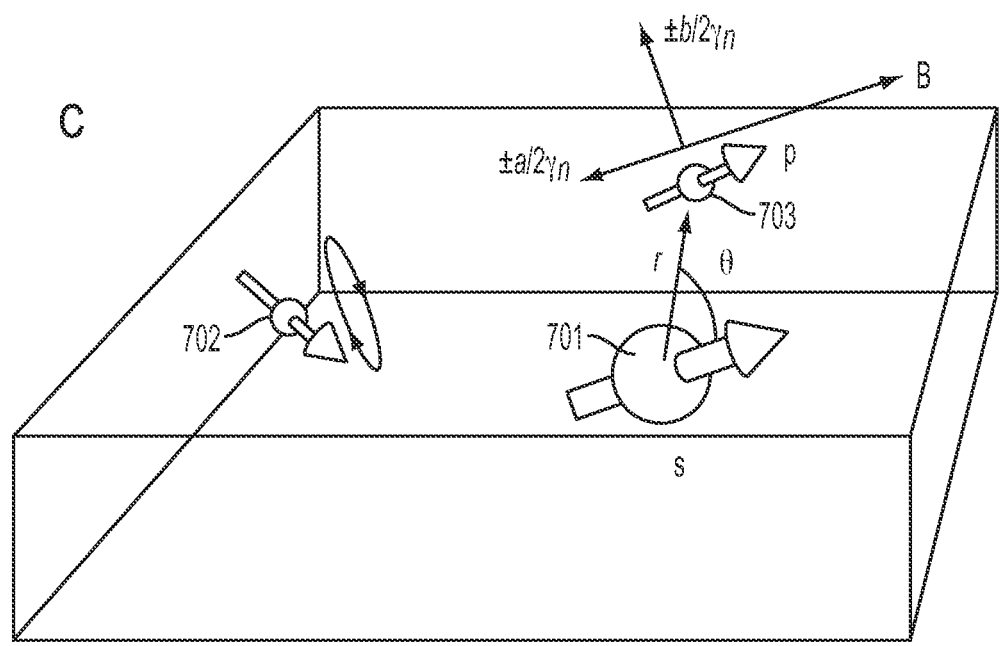
FIG. 7c is a schematic illustrating hyperfine coupling between the reporter electron spin, s (larger arrow), and the proton spins (smaller arrows)
Figure 7D:
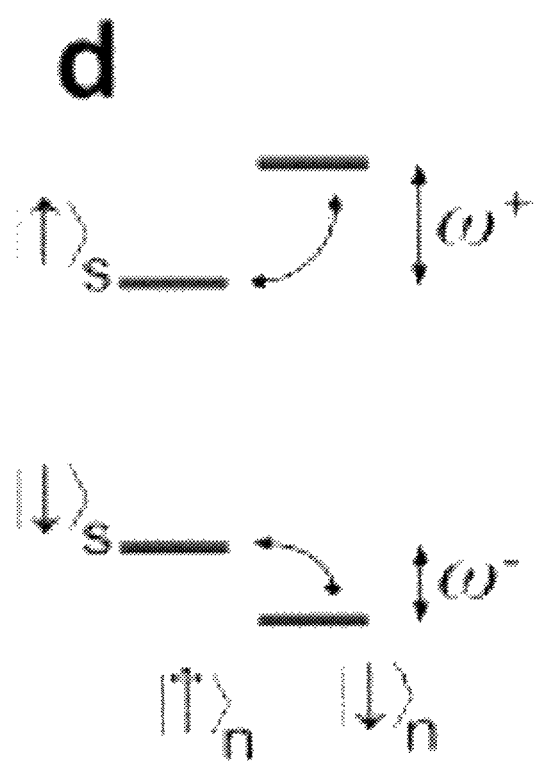
FIG. 7d shows an energy level diagram for the coupled system of the reporter spin and proximal proton spin.

To understand these observations, the coherent dynamics of a reporter electron spin interacting with proximal proton spins on the diamond surface were analyzed. The hyperfine interaction between them can be described by the Hamiltonian $H=\hbar a J_z I_z + \hbar b J_z I_x$, where J is the spin operator of the reporter qubit, I is the nuclear spin operator, and the z-axis is along the applied magnetic field. This Hamiltonian can be interpreted as an effective hyperfine field, created by the reporter spin at the site of the proton spin, as shown in FIG. 7c, which in turn gives rise to splitting of the reporter electron spin states, $\omega^\pm = \sqrt{(\pm a/2 - \omega_n)^2 + b^2/4}$, as shown in FIG. 7d. FIG. 7c is a schematic illustrating hyperfine coupling between the reporter electron spin, s, 701 (larger arrow), and the proton spins, 702 and 703 (smaller arrows). The weakly-coupled protons 702 far from the reporter spin precess in the applied magnetic field B at the Larmor frequency. The proximal proton spin, p 703, experiences the vector sum of B and the effective hyperfine fields±a/2$\gamma_n$ and ±b/2$\gamma_n$, whose signs depend on the reporter spin state. FIG. 7d shows an energy level diagram for the coupled system of the reporter spin and proximal proton spin. This level splitting causes reporter spin echo modulation at frequencies $\omega^+$ and $\omega^-$, with the modulation depth scaling as $2b\omega_n/\omega^+\omega^-$. When the proton Larmor frequency $\omega_n$ is close to half of the hyperfine interaction strength, the reporter spin echo signal is strongly modulated at $\omega^+$ and $\omega^-$, whereas the signal modulation decreases when $\omega_n$ is substantially different from a, b. Data taken at such off-resonance magnetic fields can, within their signal-to-noise ratio, be successfully described with a semiclassical nuclear spin bath model.

To analyze the experimental data quantitatively, the measurements were compared with a model that includes coherent hyperfine coupling of a reporter electron spin with a proximal proton, as well as the semiclassical spin bath of protons on the diamond surface. For NV A, the fit to the experimental data shown in FIG. 7a yields spin echo modulation frequencies of $\omega^+$=30 μs$^{-1}$ and $\omega^-$=59 μs$^{-1}$, shown as shaded squares in FIG. 6b, from which hyperfine coupling parameters a=(66±18) μs$^{-1}$ and b=(52±20) μs$^{-1}$ are extracted. Both the point magnetic dipole interaction and the contact hyperfine interaction contribute to the parameters a and b: $a=a_0+(\hbar\gamma_e\gamma_n/r_n^3)(1-3\cos^2\theta_n)$, and $b=(\hbar\gamma_e\gamma_n/r_n^3)(3\cos\theta_n\sin\theta_n)$, where $a_0$ is the contact hyperfine interaction, $r_n$ is the separation between the reporter spin and the proton spin, $\theta_n$ is the angle that the vector between them makes with the applied magnetic field. The low chemical reactivity of the reporter spins (see discussion below) suggests that the direct overlap between the reporter spin wavefunction and a surface proton is likely minimal, implying that the magnitude of $a_0$ is small. If $a_0$ is neglected, the position of the proximal proton with respect to the reporter spin most strongly coupled to NV A is $r_n$=(2.2±0.2) Å and $\theta_n$=

Figure 7E:
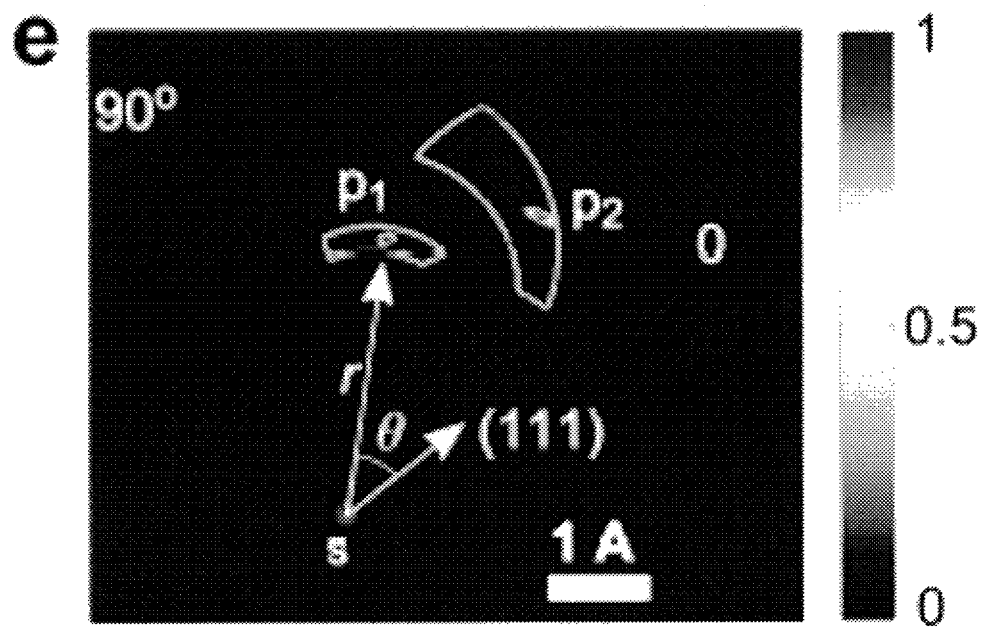
FIG. 7e shows the localization of the two proximal proton spins ($p_1$ and $p_2$) relative to the reporter spin, s, that is most strongly coupled to NV B and the color scale shows the probability density for each proton location, extracted from a fit to the data shown in (b)

(26±15°), with the azimuthal angle not quantified by the data. The data for NV B, as shown in FIG. 7b, are consistent with the presence of two proximal protons, coherently coupled to the reporter spin: their best-fit positions are $r_n^{(1)}=(2.6\pm0.2)$ Å, $\theta_n^{(1)}=(47\pm3)°$ and $r_n^{(2)}=(3.2\pm0.2)$ Å, $\theta_n^{(2)}=(19\pm4)°$, as shown in FIG. 7e in a probability density map. In order to quantify the uncertainty in the proton positions due to lack of information about the magnitude of the contact interaction, 40 μs$^{-1}$ is used as the range of possible values for $a_0$, since this is the measured contact hyperfine interaction with the OH-group proton in a hydroxylated carbon-centered radical, similar to our presumed bonding configuration (see below). For this range of $a_0$, the locations of the detected protons are constrained to be within the contours shown in FIG. 7e. It is noted that in diamond $a_0$ is likely to be much smaller due to positive electron affinity of the oxidized diamond surface.

While the origin of the reporter spins cannot be unambiguously determined from this study alone, they are likely unsaturated (or "dangling") bonds, localized near the top two carbon atom layers. It is observed that they are stable in ambient conditions over time scales of many days, which indicates that they are sterically protected from direct chemical reactions with species outside the diamond lattice. Nevertheless, the reporter spins are close to the surface, so that their position changes when exposed to the strongly-oxidizing 3-acid mixture (equal volumes of concentrated $H_2SO_4$, $HNO_3$, and $HClO_4$); furthermore they can be removed from the diamond surface by annealing the diamond at 465'C in an $O_2$ atmosphere. The detected protons are likely from covalently-bound hydroxyl (OH) and carboxyl (COOH) groups terminating the clean diamond surface under ambient conditions. Their relative locations are consistent with density-functional-theory calculations of the structure of these groups on an oxidized diamond surface.

Figure 7F:
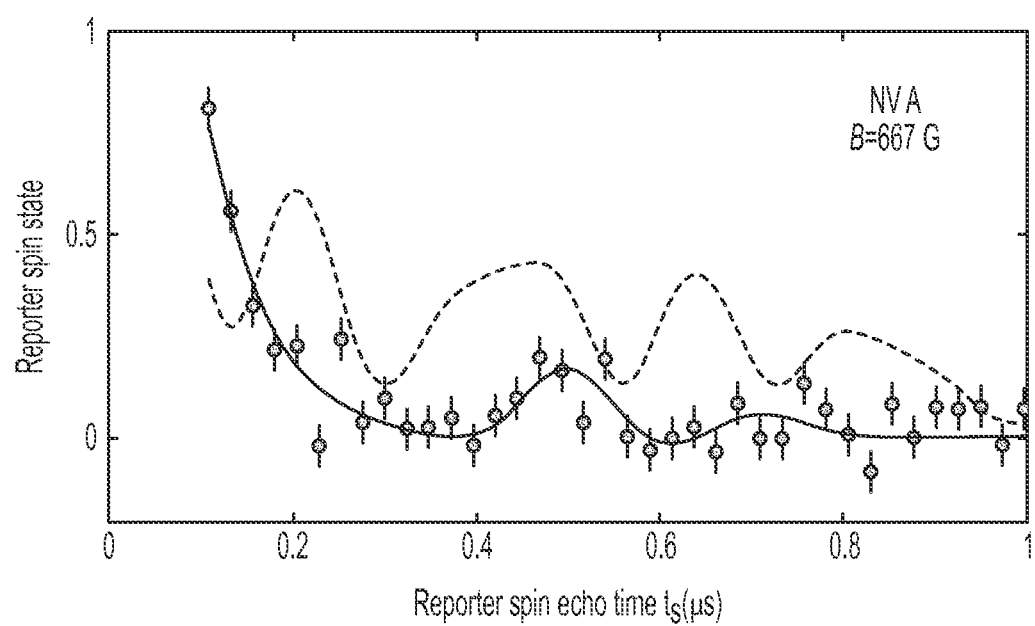
FIG. 7f shows the results of the reporter spin echo experiment on NV A after the strongly-oxidizing 3-acid mixture surface treatment.

The strongly-oxidizing 3-acid mixture surface treatment was also seen to modify the results of the reporter echo experiments as shown in FIG. 7f. FIG. 7f shows the results of the reporter spin echo experiment on NV A after this surface treatment. The data are clearly modified, indicating that this measurement is sensitive to the interaction between the reporter spin at a new, post-clean, location, with protons in its vicinity on the diamond surface.

NV centers in diamond have emerged as a nanoscale magnetic-field sensor with exquisite sensitivity under ambient conditions, enabling magnetic sensing and imaging of single electron spins and nanoscale ensembles of nuclear spins. The method disclosed here, enables magnetic resonance detection and imaging on surfaces with single nuclear spin resolution. Several other paths towards further improving the sensitivity and the broad applicability of our approach should are envisaged. It may be possible to extend the reporter spin coherence times using decoupling pulse sequences, together with dilution of the proton magnetic moments on the diamond surface, e.g. by deuteration. Individual addressing of the reporter spins may be achievable with a careful choice of the duration of the "reporter pulse sequence" readout intervals, as described above, or via frequency separation of different reporter qubits using a practical magnetic field gradient (less than 1 G/nm). Polarization transfer using, for example, Hartmann-Hahn schemes, from the NV center to the reporter spins, and possibly to strongly coupled surface nuclear spins, may allow initialization and entanglement of the surface spin network and hyper-polarization of target nuclei. The hyperfine field gradient, produced by the reporter spins, may also be used to encode spatial information for magnetic imaging. Finally, other reporter spin candidates, such as stable nitroxide radicals, can be explored, possibly providing a more flexible route for sensing applications because they can be directly attached to a reactive site of interest on a molecule under study.

NV Centers and Depth Measurements

The DEER experiments were performed on a total of 16 NV centers. 12/16 showed clear DEER collapse due to reporter spins, on the time scale shorter than their $T_2^{(nv)}$, 2/16 showed DEER collapse on the order of $T_2^{(nv)}$, and 2/16 showed no DEER collapse. NVs A and B were selected for their fastest DEER collapse, which likely means they are among the most shallow of the NV centers. Reporter sequence experiments were performed only with NVs A and B.

Figure 8:
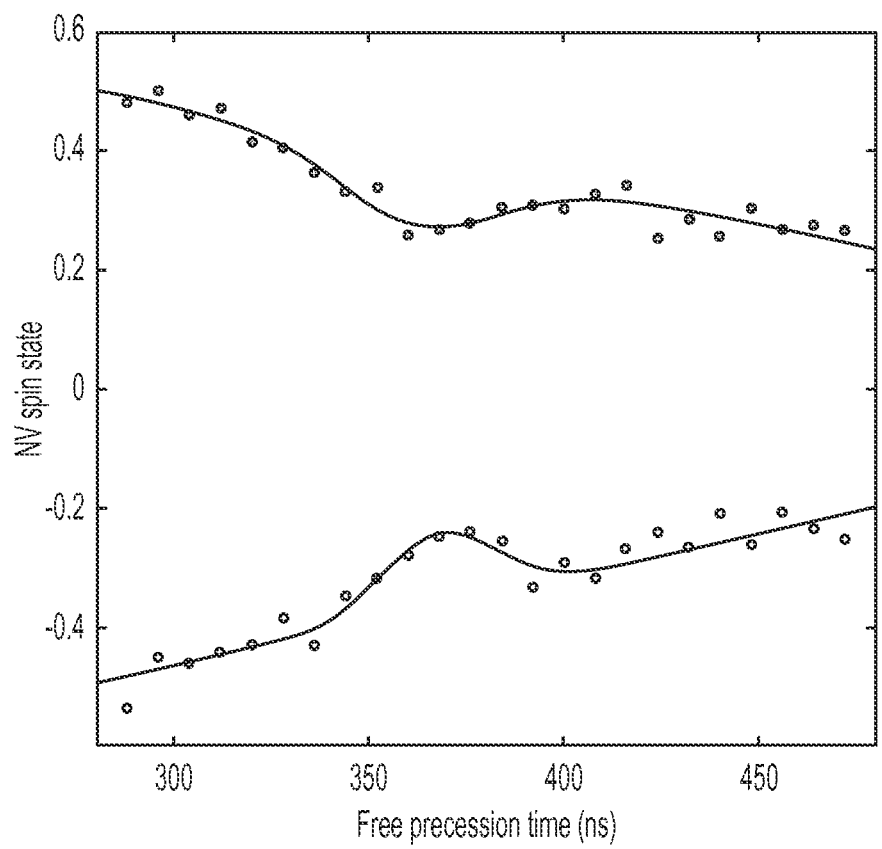
FIG. 8 shows the results of dynamical decoupling experiment (XY-16 pulse sequence) on NV A, from which its depth is extracted.

The depths of each of these two NV centers were determined by covering the diamond surface with immersion oil, and measuring the amplitude of the magnetic field created at the location of the NV center by the immersion oil proton magnetic moments, precessing at the Larmor frequency. The dynamical decoupling XY-k sequence was used to perform this ac magnetometry experiment. FIG. 8 shows the results of dynamical decoupling experiment (XY-16 pulse sequence) on NV A, from which its depth is extracted. This method yielded the following depths: NV A→(3.3±0.2) nm, and NV B→(3.6±0.3) nm.

When a separate diamond sample, with an unpolished surface, implanted and annealed with the same parameters as the one used in our work, was treated at 465° C. in an $O_2$ atmosphere, we found that the DEER signals were absent for 11 out of the 12 NV centers for which measurements were taken, and one NV center showed a "weak" DEER signal with the DEER collapse on the order of NV decoherence time $T_2^{(nv)}$. We concluded that this treatment removed the reporter spins from the diamond surface.

One skilled in the art would realize that the device and method in accordance with this disclosure, upon improvements in the coherence properties and robust control of the reporter spins, can enable a number of unique applications. NMR and MRI of individual molecules and proteins under ambient conditions is one direction that can be pursued. Quantum reporter-based sensing may also find applications in measurements of magnetic fields near complex materials, such as superconductors and topological insulators. Beyond applications in sensing and imaging, our approach provides a powerful new platform for coherent manipulation of coupled electronic and nuclear spins on surfaces or in 2D materials, which can be used to realize and explore new classes of self-assembled quantum systems.

Those skilled in the art would readily appreciate that all parameters and configurations described herein are meant to be exemplary and that actual parameters and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. The present invention is directed to each individual feature, system, or method described herein. In addition, any combination of two or more such features, systems or methods, if such features, systems or methods are not mutually inconsistent, is included within the scope of the present invention.

What is claimed is:

1. A system comprising:
a sensor, wherein, the sensor comprises,
   a network of isolated electron-spin quantum bits (qubits) disposed on the surface of the sensor; and
   a solid state electronic spin system disposed below the surface of the sensor, wherein the solid state electronic spin system has a spin-state dependent fluorescence;
a source of light;
a source of first external perturbation, wherein the source of first external perturbation generates a magnetic field;
a source of second external perturbation;
   wherein, the source of light and the first and second external perturbations are configured to coherently and independently manipulate the spin states of at least one qubit and at least one solid state electronic spin system; and
a detector to optically measure the solid-state electronic spins spin-state dependent fluorescence.

2. The system of claim 1, wherein, the sensor comprises a high purity diamond crystal lattice.

3. The system of claim 2, wherein, the solid state electronic spin system is a nitrogen-vacancy (NV) spin in the high purity diamond lattice.

4. The system of claim 1, wherein, the source of second external perturbation is a radio frequency (RF) electromagnetic field source.

5. The system of claim 1, wherein, the source of second external perturbation is an electronic spin resonance (ESR) field source.

6. The system of claim 1, wherein, the detector is a CCD camera, or a photomultiplier, or a photodiode.

7. The system of claim 1, wherein, the sample to be measured is placed in contact with the surface of the sensor.

8. The system of claim 1, wherein the sample to be measured is placed in the proximity of the sensor.

9. The system of claim 1, wherein the solid state electronic spin system interacts with one qubit.

10. The system of claim 1, wherein the solid state electronic spin system interacts with multiple qubits.

11. The system of claim 1, wherein the solid state spin systems spin-dependent fluorescence is changed due to the interaction with the qubit.

12. The system of claim 11, wherein the optically pumped laser has a wavelength of 532 nm.

13. The system of claim 1, wherein the source of light is an optically pumped laser.

14. A method of manipulating a reporter spin network and a solid state electronic spin system, comprising:
applying a first pulse sequence of external perturbation to a network of isolated electron-spin quantum bits (qubits) disposed on the surface of the sensor and a solid state electronic spin system disposed below the surface of the sensor,
   wherein the solid state electronic spin system has a spin-state dependent fluorescence;
applying a second pulse sequence of external perturbation to the network of isolated electron-spin quantum bits (qubits);
applying a third pulse sequence of external perturbation to the network of isolated electron-spin quantum bits (qubits) and a solid state electronic spin system disposed below the surface of the sensor;
wherein the first and the third pulse sequence of external perturbations probes the quantum state of at least one electronic-spin quantum bits using at least one shallow state electronic spin system; and
wherein, the quantum state of the reporter spin network is manipulated in the second pulse sequence of external perturbation.

15. The method of claim 14, further comprising comparing the qubit quantum states during the first and third pulse sequences of external perturbation.

16. The method of claim 14, further comprising controlling the length of the first and third pulse sequences of external perturbation, wherein the length of each pulse sequence of external perturbation is short enough for the change in the optical fluorescence of the solid state spins to be dominated by the coupling to the proximal most strongly coupled qubit.

17. The method of claim 14, further comprising controlling the length of the first and third pulse sequences of external perturbation, wherein the length of each pulse sequence of external perturbation is long enough for the change in the optical fluorescence of the solid state spins to be dominated by the coupling to multiple qubits.

18. The method of claim 14, wherein, the first pulse sequence of external perturbation of the solid state electronic spin systems comprises of a $\pi/2$-pulse followed by a $\pi$-pulse which is further followed by a $\pi/2$-pulse.

19. The method of claim 14, wherein, the third pulse sequence of external perturbation of the solid state electronic spin systems comprises of a $\pi/2$-pulse followed by a $\pi$-pulse which is further followed by a $\pi/2$-pulse.

20. The method of claim 14, wherein, the first pulse sequence of external perturbation of the isolated electron-spin quantum bits (qubits) comprises of a $\pi$-pulse.

21. The method of claim 14, wherein, the third pulse sequence of external perturbation of the isolated electron-spin quantum bits (qubits) comprises of a $\pi$-pulse.

22. The method of claim 14, wherein, the second pulse sequence of external perturbation of the isolated electron-spin quantum bits (qubits) comprises of a $\pi/2$-pulse, followed by a $\pi$-pulse, which is further followed by a $\pi/2$-pulse.

23. A method of sensing, coherently coupling and imaging a nuclear spin, comprising:
providing a sample containing at least one nuclear spin in proximity to a sensor;
   wherein the sensor comprises a network of isolated electron-spin quantum bits (qubits) that act as quantum reporter spins disposed on the surface of the sensor;
   and another solid state electronic spin system, wherein the solid state electronic spin system has a spin-state dependent fluorescence;
exposing the sensor to light and a first and a second external perturbation energy to coherently and independently manipulate at least one electron-spin quantum bit (qubit) and at least one solid state electronic spin system;
wherein the interaction of the nuclear spin with the qubit and the interaction of the qubit with the solid state electronic spin system changes the spin-state dependent fluorescence of the solid state electronic spin;
detecting the change in the spin-state dependent fluorescence of the solid state electronic spin system; and
inferring information regarding the nuclear spins of the sample using the detected change in the spin-state dependent fluorescence of the solid state electronic spins.

24. The method of claim 23, wherein, the sensor comprises a high purity diamond crystal lattice.

25. The method of claim 24, wherein, the solid state electronic spin system is a nitrogen-vacancy (NV) spin in the high purity diamond lattice.

26. The method of claim 23, wherein, the information inferred regarding the nuclear spins of the sample is spatial data.

27. The method of claim 23, wherein, the resolution of the detection of the nuclear spin is in the nano-length scale.

28. The method of claim 23, wherein, the second external perturbation energy comprises a radio frequency (RF) electromagnetic field.

29. The method of claim 23, wherein, the second external perturbation comprises an electronic spin resonance (ESR) field.

30. The method of claim 23, wherein, the detector is a CCD camera, or a photomultiplier, or a photodiode.

31. The method of claim 23, wherein, the sample is placed in contact with the surface of the sensor.

32. The method of claim 23, wherein, manipulating at least one electron-spin quantum bit (qubit) and at least one solid state electronic spin system comprises:
applying a first pulse sequence of external perturbation energy to the network of isolated electron-spin quantum bits (qubits) that act as quantum reporter spins disposed on the surface of the sensor and the solid state electronic spin system disposed below the surface of the sensor,
wherein the solid state electronic spin system has a spin-state dependent fluorescence;
applying a second pulse sequence of external perturbation energy to only the network of isolated electron-spin quantum bits (qubits);
applying a third pulse sequence of external perturbation to the network of isolated electron-spin quantum bits (qubits) and a solid state electronic spin system disposed below the surface of the sensor;
wherein the first and the third pulse sequence of external perturbations comprises probing the quantum state of at least one electronic-spin quantum bits using at least one solid state electronic spin system; and
wherein, the quantum state of the reporter spin network is manipulated in the second pulse sequence of external perturbation.

33. The method of claim 32, further comprising comparing the reporter-spin quantum states during the first and third pulse sequence of external perturbation.

34. The method of claim 32, further comprising controlling the length of the first and third pulse sequences of external perturbation energy, wherein the length of the pulse sequence of external perturbation is short enough for the change in the optical fluorescence of the solid state spins to be dominated by the coupling to the proximal most strongly coupled reporter spin.

35. The method of claim 32, further comprising controlling the length of the first and third pulse sequences of external perturbation energy, wherein the length of the pulse sequence of external perturbation is long enough for the change in the optical fluorescence of the solid state spins to be dominated by the coupling to multiple reporter spins.

36. The method of claim 32, wherein, the first pulse sequence of external perturbation of the solid state electronic spin systems comprises of a $\pi/2$-pulse followed by a $\pi$-pulse which is further followed by a $\pi/2$-pulse.

37. The method of claim 32, wherein, the third pulse sequence of external perturbation of the solid state electronic spin systems comprises of a $\pi/2$-pulse followed by a $\pi$-pulse which is further followed by a $\pi/2$-pulse.

38. The method of claim 32, wherein, the first pulse sequence of external perturbation of the electron-spin quantum bits (qubits) comprises of a $\pi$-pulse.

39. The method of claim 32, wherein, the third pulse sequence of external perturbation of the electron-spin quantum bits (qubits) comprises of a $\pi$-pulse.

40. The method of claim 32, wherein, the second pulse sequence of external perturbation of the electron-spin quantum bits (qubits) comprises of a $\pi/2$-pulse, followed by a $\pi$-pulse, which is further followed by a $\pi/2$-pulse.

41. The method of claim 23, wherein, a plurality of the qubits from the quantum reporter spin network are read out by a plurality of solid state electronic spin systems through the change of the spin-state dependent fluorescence.

* * * * *